US008680332B2

(12) United States Patent
Couturier et al.

(10) Patent No.: US 8,680,332 B2
(45) Date of Patent: Mar. 25, 2014

(54) DISUBSTITUTED-AMINODIFLUORO-SULFINIUM SALTS, PROCESS FOR PREPARING SAME AND METHOD OF USE AS DEOXOFLUORINATION REAGENTS

(75) Inventors: Michel A. Couturier, Sainte-Hélène-de-Breakeyville (CA); Alexandre L'Heureux, Québec (CA)

(73) Assignee: Omegachem Inc., Saint-Romuald, Québec (CA)

( * ) Notice: Subject to any disclaimer, the term of this patent is extended or adjusted under 35 U.S.C. 154(b) by 16 days.

(21) Appl. No.: 13/379,176

(22) PCT Filed: Jun. 18, 2010

(86) PCT No.: PCT/CA2010/000959
§ 371 (c)(1),
(2), (4) Date: Dec. 19, 2011

(87) PCT Pub. No.: WO2010/145037
PCT Pub. Date: Dec. 23, 2010

(65) Prior Publication Data
US 2012/0108801 A1 May 3, 2012

Related U.S. Application Data

(60) Provisional application No. 61/218,592, filed on Jun. 19, 2009, provisional application No. 61/247,703, filed on Oct. 1, 2009.

(51) Int. Cl.
*C07F 5/02* (2006.01)
(52) U.S. Cl.
USPC .................................. 564/8; 564/1; 564/102
(58) Field of Classification Search
USPC .................................. 564/1, 8, 102
See application file for complete search history.

(56) References Cited

U.S. PATENT DOCUMENTS 5,389,708 A * 2/1995 Kusumoto et al. ............ 524/137
2008/0269512 A1* 10/2008 Lovis et al. .................... 552/546

FOREIGN PATENT DOCUMENTS

WO      WO2010/145037      12/2010

OTHER PUBLICATIONS

Beaulieu et al., "Aminodifluorosulfinium Tetrafluoroborate Salts as Stable and Crystalline Deoxofluorinating Reagents," Organic Letters. vol. 11, No. 21 pp. 5050-5053 (2009).
Bezuglov et al., "Stereochemistry of Substitution of Allylic Hydroxyl with Fluorine in Prostaglandins. Synthesis of 15-Fluoro-11,15-Dideoxyprostaglandins $E_1$," Russian Journal of Bioorganic Chemistry. vol. 22, No. 10 pp. 688-695 (1996).
CAS Registry No. 83357-98-6 (Nov. 16, 1984).
CAS Registry No. 83358-00-3 (Nov. 16, 1984).
CAS Registry No. 83358-02-5 (Nov. 16, 1984).
CAS Registry No. 83358-04-7 (Nov. 16, 1984).
CAS Registry No. 83358-07-0 (Nov. 16, 1984).
CAS Registry No. 83358-09-2 (Nov. 16, 1984).
CAS Registry No. 1192487-29-8 (Nov. 16, 2009).
Cowley et al., "Amino-Substituted Sulfonium Salts, Synthesis and Stereochemistry," Journal of the American Chemical Society. vol. 100, No. 22 p. 7065-7066 (1978).
International Search Report corresponding to International Patent Application No. PCT/CA2010/000959 dated Oct. 8, 2010.
L'Heureux et al., "Aminodifluorosulfinium Salts: Selective Fluorination Reagents with Enhanced Thermal Stability and Ease of Handling," J. Org. Chem. vol. 75 pp. 3401-3411 (2010).
Lal et al., "Bis(2-methoxyethyl)aminosulfur Trifluoride: A New Broad-Spectrum Deoxofluorinating Agent with Enhanced Thermal Stability," J. Org. Chem. vol. 64, No. 19 pp. 7048-7054 (1999).
Messina et al., "Aminosulfur Trifluorides: Relative Thermal Stability [1]," Journal of Fluorine Chemistry. vol. 42 pp. 137-143 (1989).
Mews, R., and Henle, H., "Amino-Sulphur-Fluorine Derivatives as Fluoride Ion Donors: Preparation of Three- and Four-Coordinated Cations of Sulphur (IV) and (VI) (1,2)," Journal of Fluorine Chemistry. vol. 14 pp. 495-510 (1979) [Abstract].
Middleton, "New Fluorinating Reagents. Dialkylaminosulfur Fluorides," J. Org. Chem. vol. 40, No. 5 pp. 574-578 (1975).
Notification Concerning Transmittal of International Preliminary Report on Patentability (Chapter I of the Patent Cooperation Treaty) corresponding to International Patent Application No. PCT/CA2010/000959 dated Jan. 5, 2012.
Pashinnik et al., Ukr. Khim. Zh. vol. 68, No. 12 pp. 83-87 (2002) [Abstract].
Markovskiy et al., "Dialkylaminodifluorosulfone Tetrafluoroborates," Journal of Organic Chemistry. vol. 13, No. 3 pp. 1116-1117 (1977).
Pauer et al., "Fluorosulfonium Hexafluoroarsenate $RSF_2^+ AsF_6^-$," Z. Naturforsch. Chem. Sci. vol. 45b pp. 271-276 (1990).

* cited by examiner

*Primary Examiner* — Johann R Richter
*Assistant Examiner* — Pancham Bakshi
(74) *Attorney, Agent, or Firm* — Jenkins, Wilson, Taylor & Hunt, P.A.

(57) ABSTRACT

The invention relates to disubstituted-aminodifluorosulfinium salts represented by the formula (I). Processes for preparing same and methods of use as deoxofluorinating reagent is also provided.

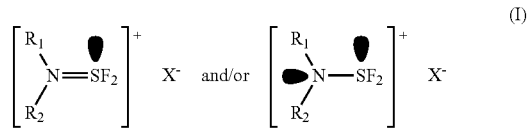

10 Claims, 7 Drawing Sheets

Fig. 1a – Type I Morphology
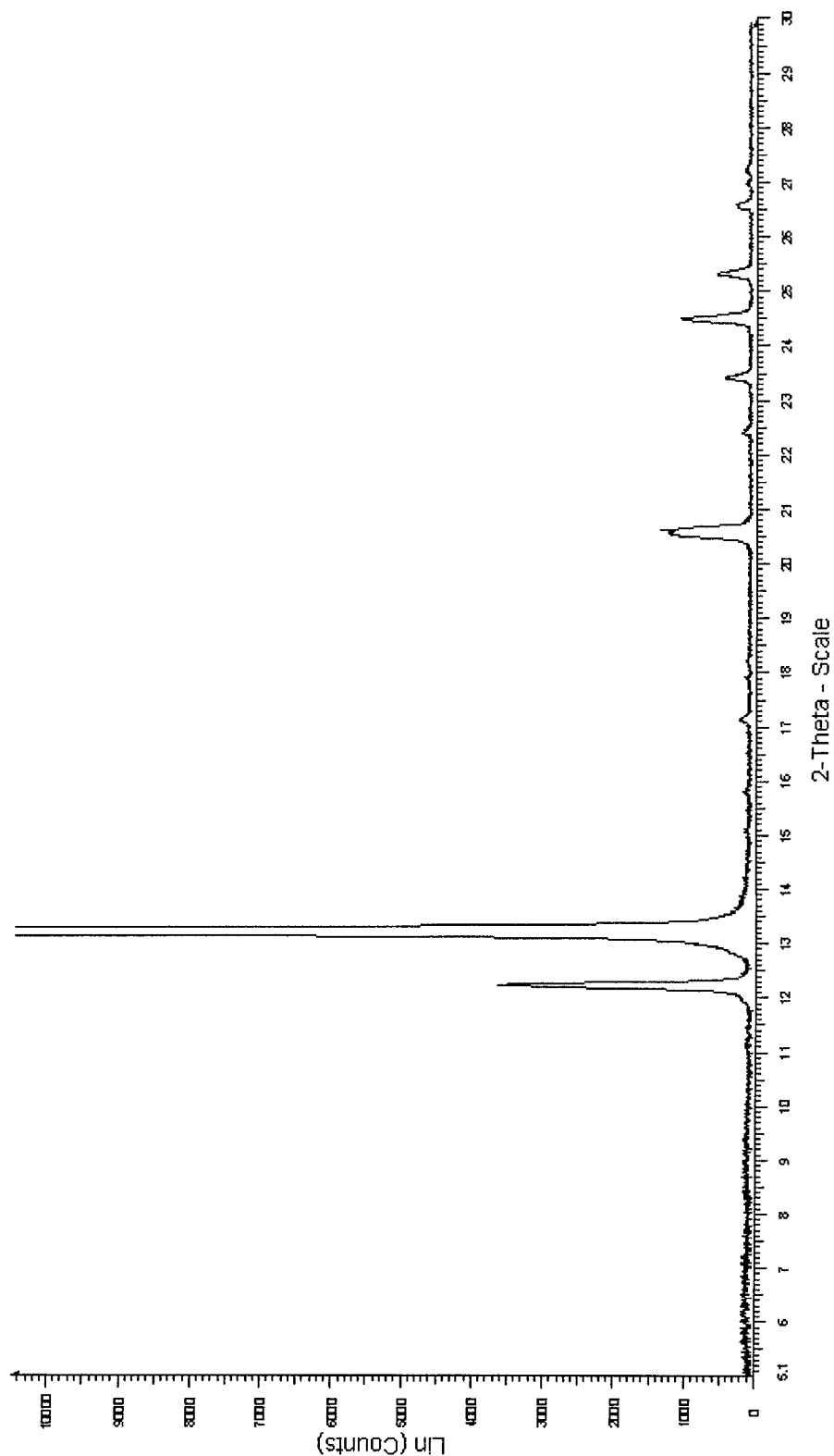

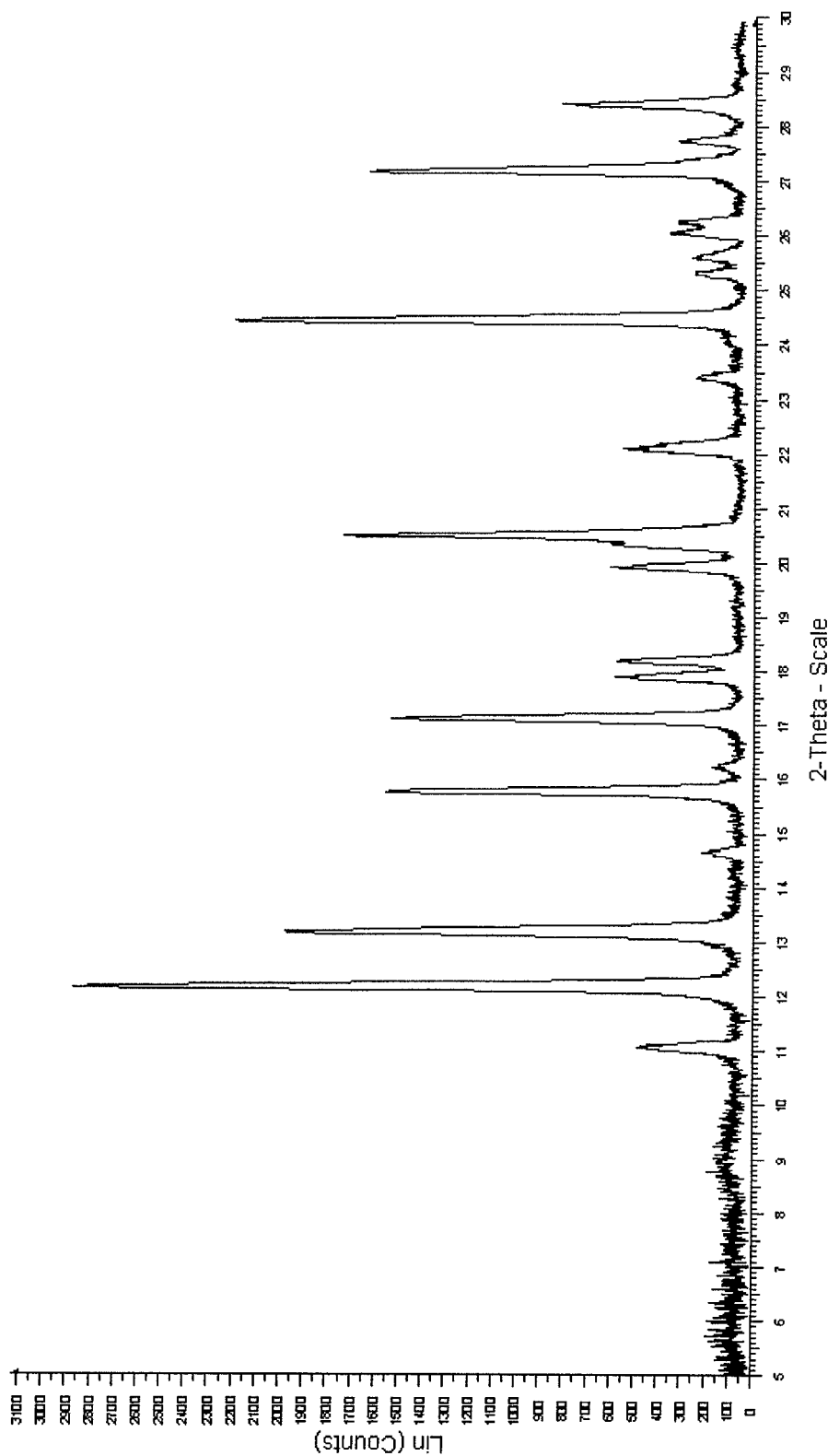
Fig. 1b – Type II Morphology

Fig. 1c – Type III Morphology
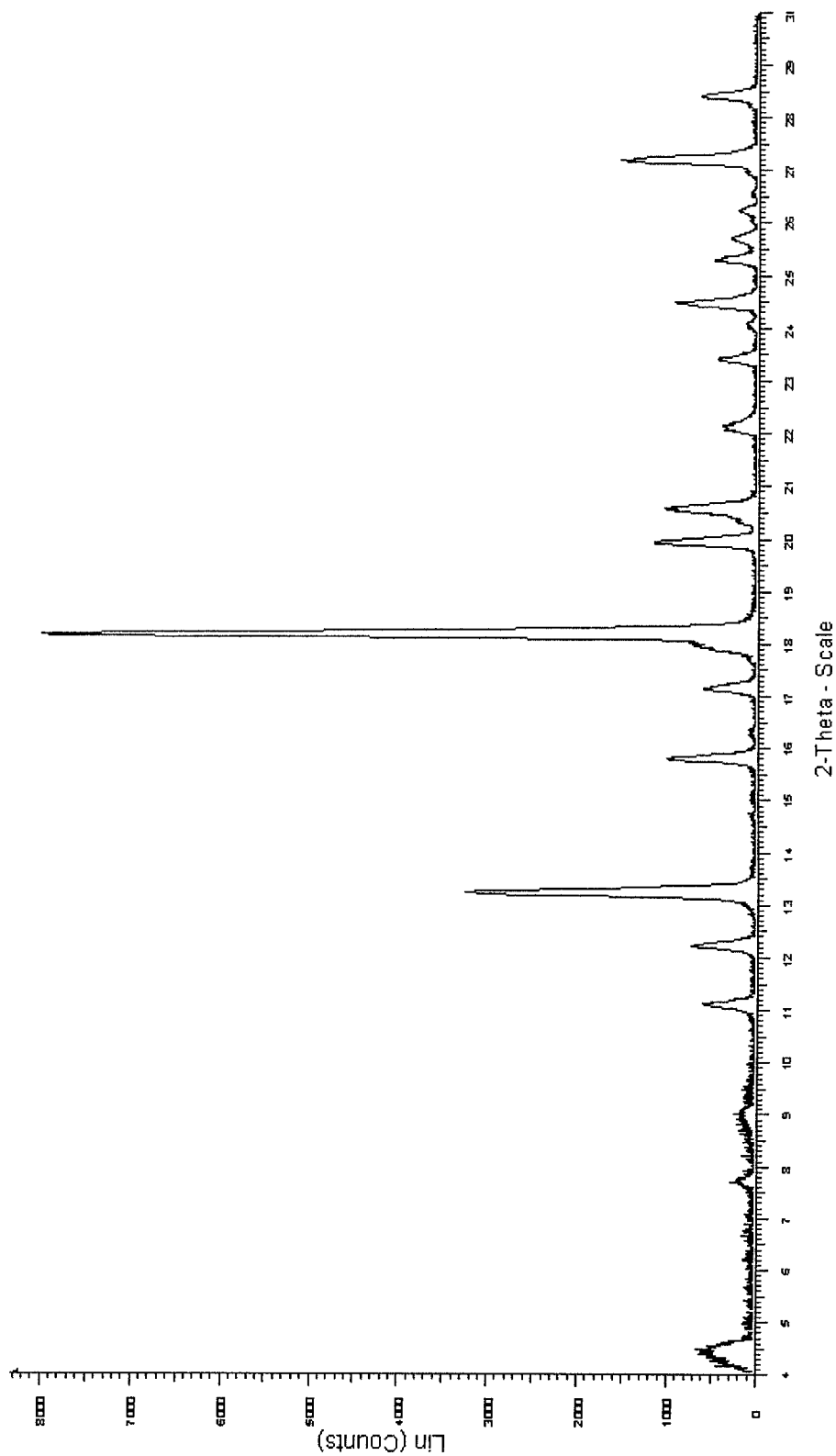

Fig. 1d – Type IV Morphology
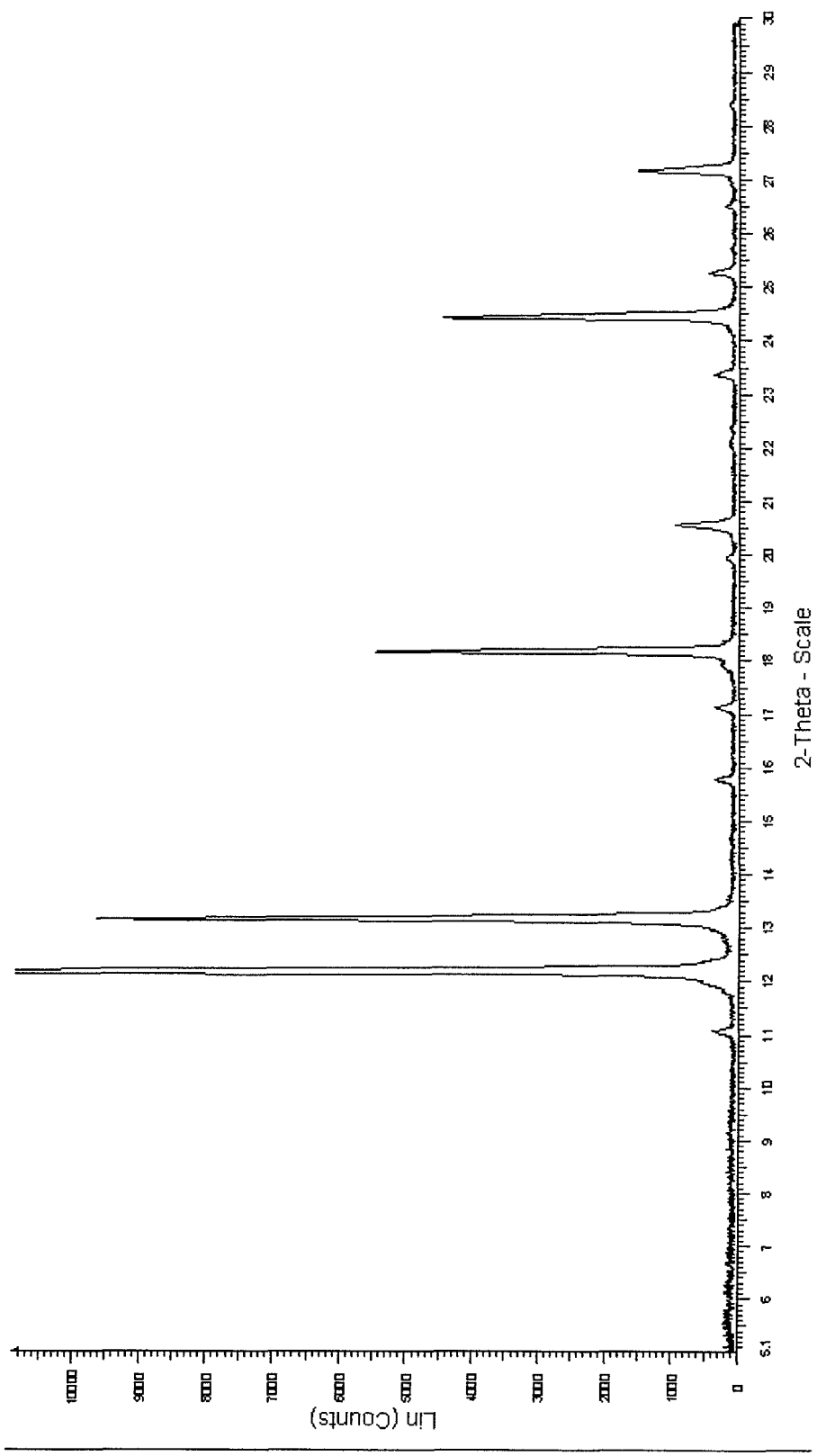

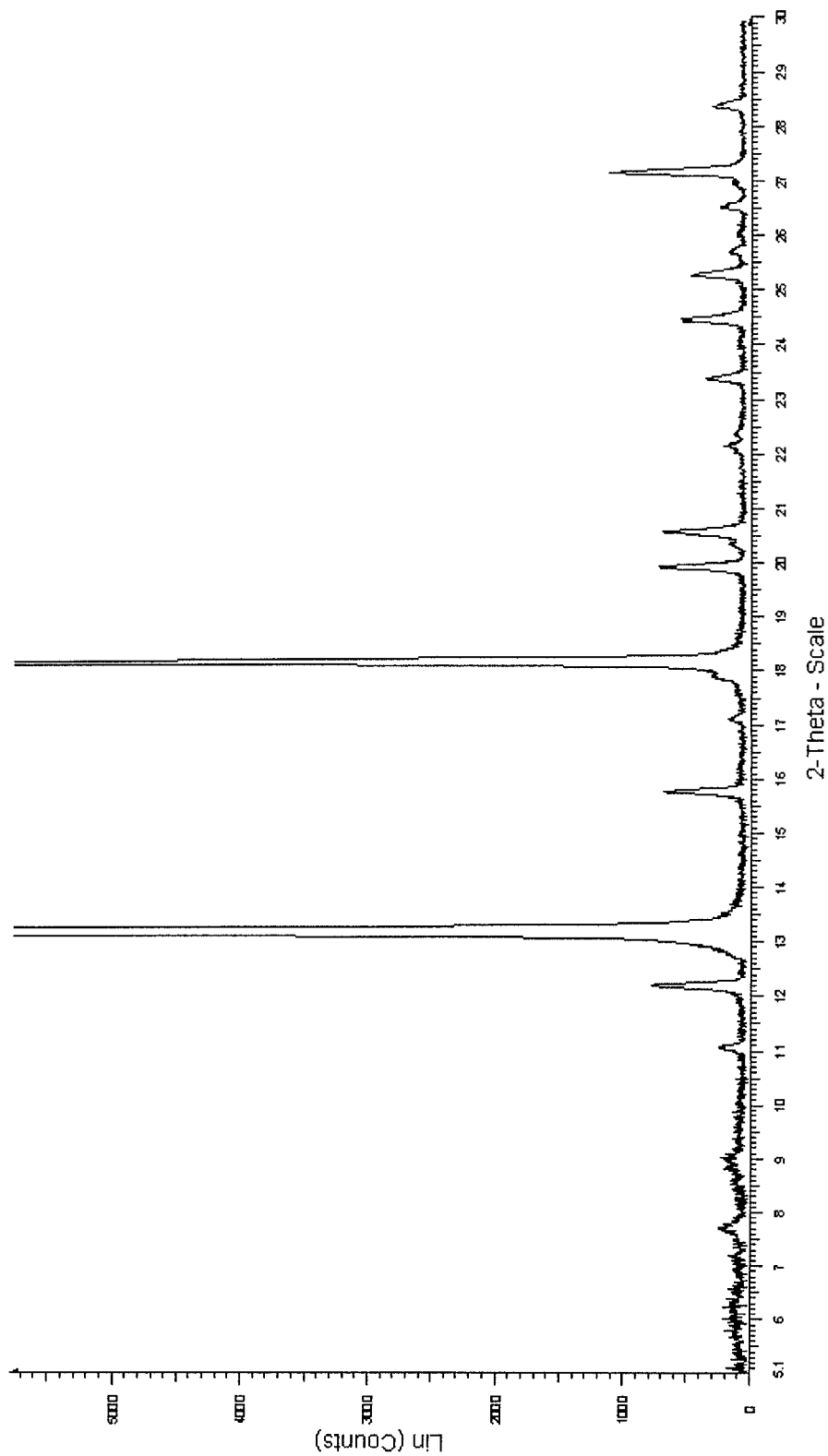
Fig. 1e – Type V Morphology

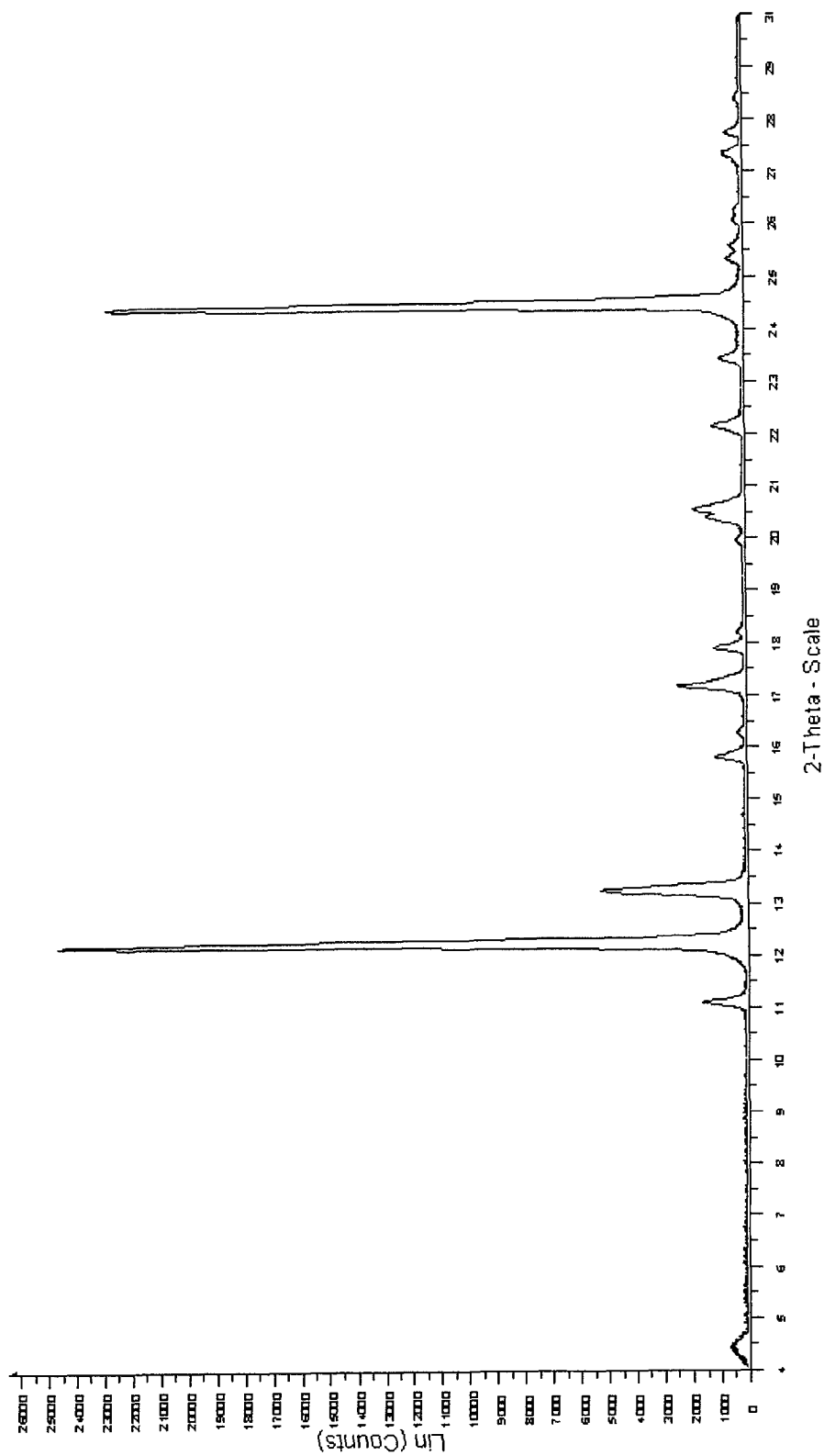
Fig. 1f – Type VI Morphology

DISUBSTITUTED-AMINODIFLUOROSULFINIUM SALTS, PROCESS FOR PREPARING SAME AND METHOD OF USE AS DEOXOFLUORINATION REAGENTS

BACKGROUND

Fluorinated compounds are of high importance in pharmaceuticals and agrochemicals since fluorinated molecules can exhibit advantageous chemical and/or biological profiles when compared with non-fluorinated analogues, for example improved stability, lipophilicity and bioavailability.

As such, there is an increasing need for safe, selective and efficient methods to introduce fluorine atoms into molecules, and a common practice is to produce fluorides from alcohols, and gem-difluorides from carbonyl functional groups, transformations which are commonly referred to as deoxofluorinations reactions.

It is known that $SF_4$ performs deoxofluorinations reactions, but in practice, handling of this highly toxic gas necessitates extensive safety measures. The reactions using $SF_4$ are often undertaken under pressure, require high temperatures (typically 100° C.) and lead to undesired side-products. In an attempt to circumvent these safety issues, various alternative fluorinating agents have been developed. Liquid diethylaminosulfur trifluoride (DAST) was developed (Middleton, W. J. *J. Org. Chem.* 1975, 40, 574), but it was later determined that this liquid was thermally unstable and highly explosive in nature (Messina, P. A.; Mange, K. C.; Middleton, W. J. *J. Fluorine Chem.* 1989, 42, 137). The manufacture of liquid DAST is also problematic as it requires purification by distillation. This purification step is hazardous, and calls for extensive safety measures and specialized equipment. This is a major cost contributor to this relatively expensive reagent.

In order to develop a safer reagent, bis(2-methoxyethyl) aminosulfur trifluoride (Deoxo-Fluor®) was developed (Lal, G. S.; Pez, G. P.; Pesaresi, R. J.; Prozonic, F. M.; Cheng, H. *J. Org. Chem.* 1999, 71, 7048). It has been reported by differential scanning calorimetry (DSC) that DAST and Deoxofluor® have the same decomposition temperature, but DAST degrades more rapidly with somewhat larger heat evolution.

Whilst Deoxo-Fluor is an adequate substitute for DAST and is indeed less explosive than DAST there are occasions when it remains necessary to use DAST. Thus, and in addition to the aforementioned safety issues there are other significant problems associated with the use of DAST, Deoxo-Fluor and related dialkylaminosulfur trifluoride reagents. Said reagents are fuming liquids difficult to handle in humid environments and react violently with water. Thereby, such reagents do not lend themselves to large scale fluorination processes. The liquids also discolor with aging, and since they have been seen to degrade on storage they sometimes require re-distillation to be satisfactory for use. Furthermore, their explosiveness necessitates strict shipping restrictions and strict legal provisions with respect to their storage and handling.

Salt derivatives of dialkylaminosulfur trifluoride have been known for over three decades. Markovskii et al. were the first to report examples of dialkylaminodifluorosulfinium salts (Markovskii, L. N.; Pashinnik, V. E.; Saenko, E. P. *Zh. Org. Khim.* 1977, 13, 1116). They describe the reaction of $BF_3.Et_2O$ with diethylaminosulfurtrifluoride or one of its dimethylamino, piperidino or morpholino analogues to produce the corresponding tetrafluoroborate salt. Later, Cowley et al. (Cowley, A. H.; Pagel, D. J.; Walker, M. L. *J. Am. Chem. Soc.* 1978, 100, 7065) and Mews and Henle (Mews, R.; Henle, H. *J. Fluorine Chem.* 1979, 14, 495) reported that other Lewis acid could be used by contacting dimethylaminosulfur trifluoride with $BF_3$, $PF_5$ and $AsF_5$ to form the corresponding dimethylaminodifluorosulfinium salts. The structure of dialkylaminosulfinium salt has been more understood with the further studies of Pauer et al. (Pauer, F.; Erhart, M.; Mews, R.; Stalke, D. *Z. Naturforsch., B: Chem. Sci.* 1990, 45, 271) in which they have resolved the crystal structure of dimethylaminodifluorosulfinium hexafluoroarsenate. Recently another dialkylaminosulfinium salt has been discovered when Pashinnik et al. (Pashinnik, V. E.; Martynyuk, E. G.; Shermolovich, Y. G. *Ukr. Khim. Zh.* 2002, 68, 83) reported that morpholinosulfur trifluoride reacts with $SeF_4$ to form morpholinodifluorosulfinium pentafluoroselenate. Although some dialkylaminosulfinium salts have been isolated and characterized, little is known with respect to their chemical reactivity. However, one example of the use of a salt in a deoxofluorination reaction was reported over a decade ago by Pashinnik et al. (Bezuglov, V. V.; Pashinnik, V. E.; Tovstenko, V. I.; Markovskii, L. N.; Freimanis, Y. A.; Serkov, I. V. *Russ. J. Bioorg. Chem.* 1996, 22, 688) whereby the reaction of an allylic alcohol in a prostaglandin with morpholinodifluorosulfinium tetrafluoroborate in acetonitrile was reported.

Thus, it is clear that there remains a need for safe and effective fluorinating agents which are inexpensive and can be manufactured with relative ease.

The present inventors have published the following reports: Beaulieu, F.; Beauregard, L.-P.; Courchesne, G.; Couturier, M.; LaFlamme, F.; L'Heureux, A. *Org. Lett.* 2009, 11, 5052; L'Heureux, A.; Beaulieu, F.; Bennett, C.; Bill, D. R.; Clayton, S.; LaFlamme, F.; Mirmehrabi, M.; Tadayon, S.; Tovell, D.; Couturier, M *J. Org. Chem.* 2010, 75, 3401, wherein some details are presented in respect of the present invention.

SUMMARY

In one aspect of the present invention, there is provided an isolated solid of a disubstituted-aminodifluorosulfinium salt represented by the formula:

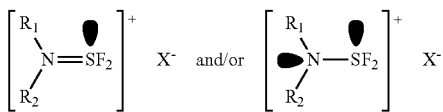

wherein $R_1$ and $R_2$ are independently selected from the group consisting of alkyl, aryl, aralkyl, heterocycle and heteroaryl, each of which is optionally substituted or $R_1$ and $R_2$ form together an optionally substitute alkylene chain of 4-6 carbon atoms which optionally comprises one or more heteroatoms selected from N, S and O; and $X^-$ is a counterion, provided that said disubstituted-aminodifluorosulfinium salt is other than:
dimethylaminodifluorosulfinium tetrafluoroborate
diethylaminodifluorosulfinium tetrafluoroborate (needles; m.p. 74-76° C.)
piperidinodifluorosulfinium tetrafluoroborate (needles; m.p. 92-94° C.)
morpholinodifluorosulfinium tetrafluoroborate (prisms; m.p. 104-106° C.)
and when $R_1$ and $R_2$ are both dimethyl, then $X^-$ is other than $SbF_6^-$, $PF_6^-$, and $AsF_6^-$, and when $R_1$ and $R_2$ form a morpholino residue together with the nitrogen to which they are attached then $X^-$ is other than $SeF_5^-$.

In one aspect, there is provided an isolated solid of a disubstituted-aminodifluorosulfinium trifluoromethanesulfonate salt represented by the formula:

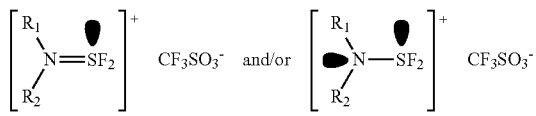

wherein $R_1$ and $R^2$ are independently selected from the group consisting of alkyl, aryl, aralkyl, heterocycle and heteroaryl, each of which is optionally substituted; or $R_1$ and $R_2$ form together an optionally substituted alkylene chain of 4-6 carbon atoms which optionally comprises one or more heteroatoms selected from N, S and O.

In one aspect, there is provided an isolated solid of a disubstituted-aminodifluorosulfinium tetrafluoroborate salt represented by the formula:

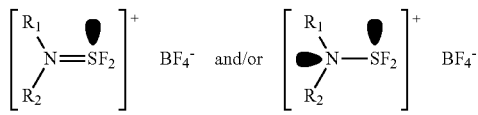

wherein $R_1$ and $R_2$ are independently selected from the group consisting of alkyl, aryl, aralkyl, heterocycle and heteroaryl, each of which is optionally substituted or $R_1$ and $R_2$ form together an optionally substituted alkylene chain of 4-6 carbon atoms which optionally comprises one or more heteroatoms selected from N, S and O; excluding:
dimethylaminodifluorosulfinium tetrafluoroborate
diethylaminodifluorosulfinium tetrafluoroborate (needles; m.p. 74-76° C.)
piperidinodifluorosulfinium tetrafluoroborate (needles; m.p. 92-94° C.) and
morpholinodifluorosulfinium tetrafluoroborate (prisms; m.p. 104-106° C.).

In one aspect, there is provided diethylaminodifluorosulfinium tetrafluoroborate morphologies type II, III, IV, V and VI.

In one aspect, there is provided morpholinodifluorosulfinium tetrafluoroborate morphology type II.

In one aspect, there is provided a mixture of diethylaminodifluorosulfinium tetrafluoroborate comprising at least two morphologies of diethylaminodifluorosulfinium tetrafluoroborate as defined herein.

In a further aspect, there is provided a method for preparing an isolated solid of a disubstituted-aminodifluorosulfinium salts represented by the formula

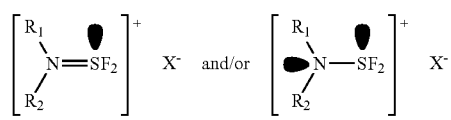

comprising contacting a disubstituted-aminosulfur trifluoride of formula $R_1R_2N$—$SF_3$ with a strong Bronsted acid, wherein $R_1$ and $R_2$ are independently selected from the group consisting of alkyl, aryl, aralkyl, heterocycle and heteroaryl, each of which is optionally substituted; or $R_1$ and $R_2$ form together an optionally substituted alkylene chain of 4-6 carbon atoms which optionally comprises one or more heteroatoms selected from N, S and O; and $X^-$ is a conjugate base of a strong Bronsted acid.

In one aspect, there is provided a method for preparing an isolated solid of a disubstituted-aminodifluorosulfinium tetrafluoroborate salt represented by the formula:

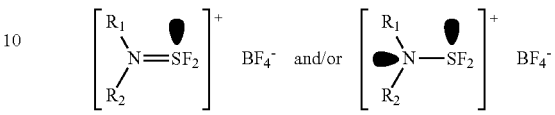

comprising contacting unpurified disubstituted-aminosulfur trifluoride of formula $R_1R_2N$—$SF_3$ with a source of $BF_3$ or $HBF_4$, wherein $R_1$ and $R_2$ are as defined herein.

In a further aspect there is provided a method for the deoxofluorination of a compound comprising at least one functional group selected from the group consisting of —OH, =O, —COOH and mixtures thereof, said method comprising contacting said compound with a disubstituted-amino difluorosulfinium salt represented by the formula:

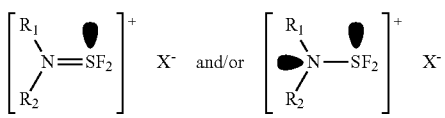

and with an exogenous fluoride sources of ionic fluoride, wherein $R_1$ and $R_2$ are independently selected from the group consisting of alkyl, aryl, aralkyl, heterocycle and heteroaryl, each of which is optionally substituted; or $R_1$ and $R_2$ form together an optionally substituted alkylene chain of 4-6 carbon atoms which optionally comprises one or more heteroatoms selected from N, S and O and $X^-$ is a counterion.

In a further aspect there is provided a method for the deoxofluorination of a compound comprising at least one functional group selected from the group consisting of —OH, —COOH and mixtures thereof, said method comprising contacting said compound with a disubstituted-amino difluorosulfinium salt represented by the formula:

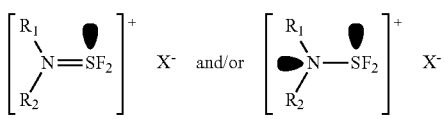

and with a base, wherein $R_1$ and $R_2$ are independently selected from the group consisting of alkyl, aryl, aralkyl, heterocycle and heteroaryl, each of which is optionally substituted or $R_1$ and $R_2$ form together an optionally substituted alkylene chain of 4-6 carbon atoms which optionally comprises one or more heteroatoms selected from N, S and O; and $X^-$ is a counterion.

DESCRIPTION OF THE FIGURES

FIG. 1a is an XRD of a polymorph described in the prior art;

FIGS. 1b-1f are XRDs of different morphologies in accordance with embodiments of the disclosure;

DETAILED DESCRIPTION

Figure 2:
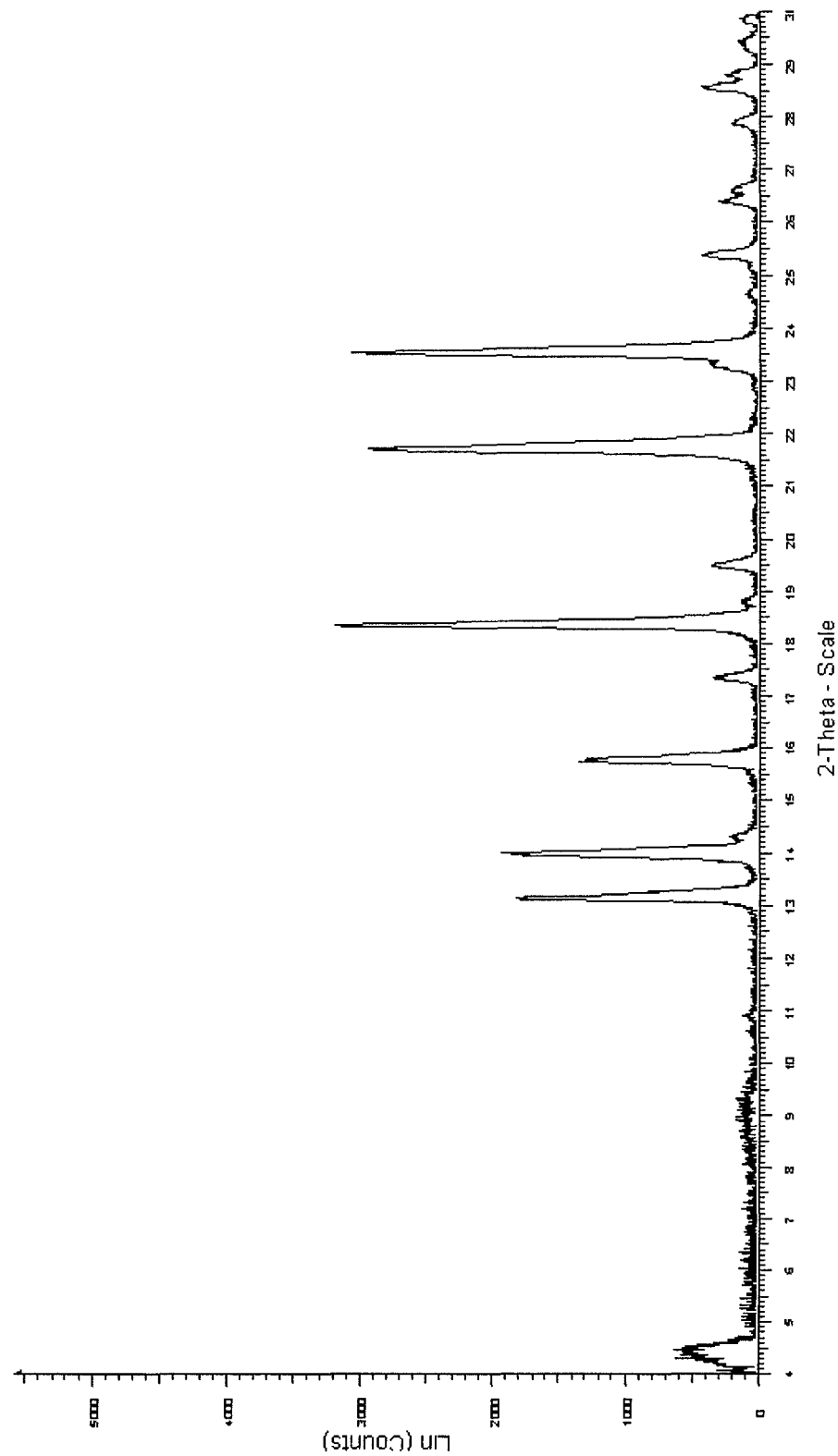
FIG. 2 is an XRD of a new polymorph in accordance with one embodiment of the disclosure.

The term "alkyl" represents a linear, branched or cyclic (including polycyclic) hydrocarbon moiety having from 1 to 18 carbon atoms, preferably from or 1 to 12 carbon atoms, more preferably 1 to 10 carbon atoms and most preferably from 1 to 6 carbon atoms, provided that a cyclic moiety contains at least 3 carbon atoms and preferably up to 18 carbon atoms, and each of these can be optionally substituted. Examples include but are not limited to optionally substituted methyl, ethyl, propyl, isopropyl, butyl, isobutyl, sec-butyl, tert-butyl, pentyl, isopentyl, neopentyl, tert-pentyl, hexyl, isohexyl, neohexyl, cyclopropyl, cyclobutyl, cyclopentyl and cyclohexyl. The term "alkyl" as used herein is also meant to include alkyls in which one or more hydrogen atom is replaced by a halogen, i.e. an alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl which are in turn optionally substituted.

The term "alkylene" represent a divalent "alkyl" group.

The term "alkenyl" represents an alkyl chain of 2 to 12 carbon which has one or more double bond in the chain and is optionally substituted.

The term "alkynyl" represents an alkyl chain of 2 to 12 carbons which has one or more triple bond in the chain and is optionally substituted.

The term "alkoxy" represents an alkyl which is covalently bonded to the adjacent atom through an oxygen atom. Examples include but are not limited to methoxy, ethoxy, propyloxy, isopropyloxy, butoxy, tert-butyloxy, cyclopropyloxy, cyclobutyloxy, cyclopentyloxy and cyclohexyloxy.

The term "alkylthio" represents an alkyl which is covalently bonded to the adjacent atom through a sulfur atom. Examples include but are not limited to methylthio, ethylthio, propylthio, isopropylthio, butylthio, tert-butylthio, cyclopropylthio, cyclobutylthio, cyclopentylthio and cyclohexylthio.

The term "alkylamino" represents an alkyl which is covalently bonded to the adjacent atom through a nitrogen atom and may be monoalkylamino or dialkylamino, wherein the alkyl groups may be the same or different. Examples include but are not limited to methylamino, ethylamino, propylamino, isopropylamino, butylamino, tert-butylamino, cyclopropylamino, cyclobutylamino, cyclopentylamino and cyclohexylamino.

The term "aralkyl" represents an aryl group attached to the adjacent atom by a C1-6 alkyl. Examples include but are not limited to benzyl, benzhydryl, trityl, phenethyl, 3-phenylpropyl, 2-phenylpropyl, 4-phenylbutyl and naphthylmethyl.

The term "aryl" represents a carbocyclic moiety containing at least one benzenoid-type ring (i.e. may be monocyclic or polycyclic) having 6 to 10 carbon atoms, and which may be optionally substituted with one or more substituents. Examples include but is not limited to phenyl, tolyl, dimethylphenyl, aminophenyl, anilinyl, naphthyl, anthryl, phenanthryl or biphenyl.

The term "heterocycle" represents a 3 to 10 membered optionally substituted saturated, unsaturated cyclic moiety wherein said cyclic moeity comprises at least one heteroatom selected from oxygen (O), sulfur (S) or nitrogen (N). Embodiments include heterocycles of 3 to 6 membered ring or 5 to 6 membered ring. Heterocycles may be monocyclic or polycyclic rings. Examples include but are not limited to Aziridine, Oxirane, Thiirane, Pyrrolidine, Tetrahydrofuran, Dihydrofuran, Tetrahydrothiophene, Piperidine, Tetrahydropyran, Thiane, Azepane, Oxepane and Thiepane. Heterocycles include rings systems that are formally derived by fusion with other rings, such as benzo-fused rings including indane and di- and tetra-hydro-quinolines, di- and tetra-hydro-isoquinolines and benzazepines.

The term "heteroaryl" represents a 5 to 12 membered optionally substituted aromatic cyclic moiety wherein said cyclic moeity comprises at least one heteroatom selected from oxygen (O), sulfur (S) or nitrogen (N). Embodiments include heteroaryl of 5 to 6 membered monocyclic or 10 to 12 polycyclic rings. Examples include but are not limited to Pyrrole, Furan, Thiophene, Pyridine, Azepine, indole, isoindole, quinoline and isoquinolines The term "counterion" is meant to include ion that accompanies the disubstituted-aminodifluorosulfinium moiety in order to maintain electric neutrality. The counterion can be obtained from the reaction between a fluoride ion acceptor, such as $BF_3$, $SbF_5$, $PF_5$, $AsF_5$, $SeF_4$, with a disubstituted-aminosulfur trifluoride of formula $R_1R_2N-SF_3$ wherein $R_1$ and $R_2$ are as defined herein. Examples of counterion as used herein include but are not limited to $BF_4^-$, $SbF_6^-$, $PF_6^-$, $AsF_6^-$, $SeF_5^-$. The counterion can also be the conjugate base of a strong Bronsted acid. In one embodiment, the Bronsted acid is trifluoromethanesulfonic acid (TfOH) or tetrafluoroboric acid including $HBF_4$ etherate, $HBF_4$ dimethyl ether complexes.

The term "unpurified" in relation to disubstituted-aminosulfur trifluoride of formula $R_1R_2N-SF_3$ means a crude reaction mixture, e.g. non-distilled, reagent obtained when preparing said compound of formula $R_1R_2N-SF_3$.

The term "independently" means that substituents can be the same or a different definition for each item.

The term "substituent" as used herein or the substituent inherent to the expression "optionally substituted" means but not limited to halogen, alkoxy, amino including primary and secondary amino, amidino, amido, azido, cyano, guanido, nitro, nitroso, urea, sulfate, sulfite, sulfonate, sulphonamide, phosphate, phosphonate, alkylthio or alkylamino, alkenethio or alkeneamino, alkynethio or alkyneamino, protected hydroxy group, protected amino group, ester or amido derivatives of —COOH, protected =O such as ketal and hemiketal.

The term "exogenous promoters" means a chemical additive that is contributing to the deoxofluorination reaction. Examples include exogenous fluoride source or a base (organic or inorganic).

In one embodiment, the deoxofluorinating reagents described herein provide at least one of the following feature: increased thermal stability, increased stability towards atmospheric moisture and have less stringent shipping restrictions.

In one embodiment, the method of producing deoxofluorination reagents described herein provide at least one of the following feature: cost efficiency, avoiding the need for a distillation and the deoxofluorination reagents can be isolated by simple filtration.

In one embodiment, the use of reagents described herein for conducting deoxofluorination provides at least one of the feature: No generation of free HF during the fluorination reaction under anhydrous conditions; less formation of elimination side products and safer use from a termal safety perspective In one embodiment, there is provided new disubstituted-aminodifluorosulfinium salts and/or polymorphic types which have been found to be surprisingly storage and/or thermally stable under typical storage/processing conditions. In one embodiment, the disubstituted-aminodifluorosulfinium salt is isolated as a solid. In a further embodiment, the disubstituted-aminodifluorosulfinium salt is isolated as a crystalline solid. Disubstituted-aminodifluorosulfinium salt in accordance with the disclosure may include tautomers. Disubstituted-amino difluorosulfinium salt includes isolated or non-isolated single tautomeric forms or mixtures of same in all proportions.

In one embodiment, there is provided an isolated solid of a disubstituted-aminodifluorosulfinium trifluoromethanesulfonate salt represented by the formula:

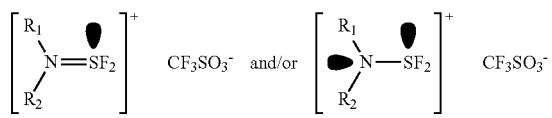

wherein $R_1$ and $R_2$ are independently selected from the group consisting of alkyl, aryl, aralkyl, heterocycle and heteroaryl, each of which is optionally substituted. In still a further embodiment, $R_1$ and $R_2$ form together an alkylene chain of 4-6 carbon atoms which optionally comprises one or more heteroatoms selected from N, S and O.

In further embodiments, in all occurrences of disubstituted-aminodifluorosulfinium salts defined herein:

$R_1$ and $R_2$ are independently selected from the group consisting of alkyl, aryl, aralkyl, heterocycle and heteroaryl, each of which is optionally substituted;

$R_1$ and $R_2$ form together an alkylene chain of 4-6 carbon atoms which optionally comprises one or more heteroatoms selected from N and O.

$R_1$ and $R_2$ are the same or different and are alkyl of 1 to 3 carbon atoms, aryl of 6 to 10 carbon atoms, 6-membered heteroaryl wherein the heteroatom is nitrogen (N);

$R_1$ and $R_2$ are the same or different and are methyl, ethyl, propyl, isopropyl, butyl, isobutyl, sec-butyl, cyclopropyl, cyclobutyl, cyclopentyl, cyclohexyl, phenyl, pyridinyl, 2-methoxyethyl, $R_1$ and $R_2$ are both methyl; $R_1$ and $R_2$ are both ethyl; $R_1$ and $R_2$ are both 2-methoxyethyl;

R1 is methyl and R2 is phenyl; R1 is methyl and R2 is pyridinyl; R1 is methyl and R2 is benzyl;

$R_1$ and $R_2$ form together with the nitrogen atom to which they are attached:

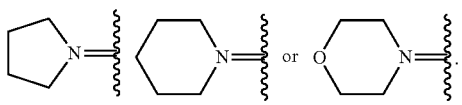

Applicant has observed that DAST reacts exothermically with a strong Bronsted acid such as tetrafluoroboric acid to provide dialkylaminodifluorosulfinium tetrafluoroborate and HF as described below. This finding constitutes a novel method for the preparation of dialkylaminodifluorosulfinium salts. Insofar, the previously reported dialkylaminodifluorosulfinium salts were prepared via fluorination of $BF_3$, $PF_5$, $AsF_5$, $SeF_4$, $SbF_5$, and the types of salts were limited to the corresponding counteranions. Advantageously, other types of counterions are accessible via this approach. In another example described below, diethylaminodifluorosulfinium trifluoromethanesulfonate salt can be readily prepared by contacting DAST with triflic acid. Applicant has also found that triflic anhydride could be used instead of triflic acid to produce triflate salts.

In one embodiment, there is provided a method for preparing a an isolated solid of a disubstituted-aminodifluorosulfinium salt represented by the formula:

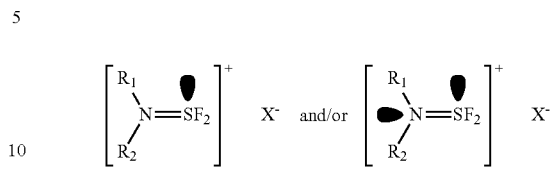

comprising contacting a disubstituted-aminosulfur trifluoride of formula $R_1R_2N$—$SF_3$ with a strong Bronsted acid, wherein $R_1$ and $R_2$ are as defined herein and $X^-$ is a conjugate base of a strong Bronsted acid.

In one embodiment, there is provided a method for preparing an isolated solid of a disubstituted-aminodifluorosulfinium tetrafluoroborate salts represented by the formula:

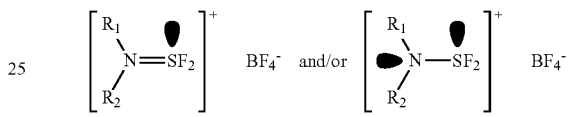

comprising contacting a disubstituted-aminosulfur trifluoride of formula $R_1R_2N$—$SF_3$ with a source of tetrafluoroboric acid, wherein $R_1$ and $R_2$ are as defined herein.

In one embodiment, there is provided a method for preparing an isolated solid of a disubstituted-aminodifluorosulfinium trifluoromethane sulfonate salts represented by the formula:

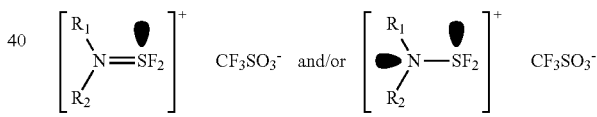

comprising contacting a disubstituted-aminosulfur trifluoride of formula $R_1R_2N$—$SF_3$ with trifluoromethanesulfonic acid, wherein $R_1$ and $R_2$ are as defined herein.

In one embodiment, there is provided a method for preparing a crystalline disubstituted-aminodifluorosulfinium tetrafluoroborate comprising contacting an unpurified DAST reagent or the like with a source of $BF_3$ or $HBF_4$. In one embodiment, the crystalline product can be isolated via filtration. It is observed that isolating a crystalline product eliminates the need for potentially time consuming, costly and hazardous distillation of DAST reagent or the like. Such a derivative would be desirable both form a handling and manufacturing standpoint.

In one embodiment, the source of $BF_3$ is $BF_3$ gas or a complex selected from the group consisting of $BF_3$ etherate, $BF_3$ tetrahydrofuran complex and $BF_3$ acetonitrile complex. The source of $HBF_4$ can be a complex selected from the group consisting of $HBF_4$ etherate and $HBF_4$ dimethyl ether complex.

In one embodiment, there is provided a method for preparing an isolated solid of a disubstituted-aminodifluorosulfinium tetrafluoroborate salt represented by the formula:

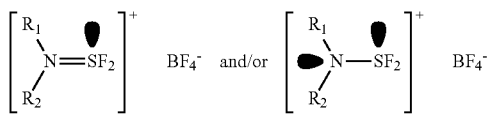

comprising contacting unpurified disubstituted-aminosulfur trifluoride of formula R₁R₂N—SF₃ with a source of BF₃, or HBF₄ wherein R₁ and R₂ are as defined herein. In a further embodiment, the disubstituted-aminosulfur trifluoride is prepared from a disubstituted-trimethylsilylamine and SF₄, or from the corresponding disubstituted-amine, a trisubstituted amine and SF₄.

In one embodiment, the disubstituted-aminodifluorosulfinium salt as described herein are prepared in the presence of a halocarbon solvent, an ether solvent or mixtures thereof.

In one embodiment, the disubstituted-aminodifluorosulfinium salt as described herein are prepared from a crude reaction mixture of disubstituted-aminosulfur trifluoride in a one pot process.

In a further embodiment there is provided a method for the deoxofluorination of a compound comprising at least one functional group selected from the group consisting of —OH, ═O, —COOH and mixtures thereof, said method comprising contacting said compound with a disubstituted-amino difluorosulfinium salt represented by the formula:

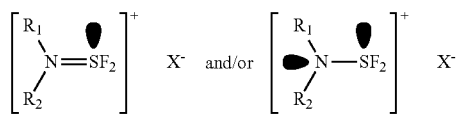

with an exogenous fluoride sources of ionic fluoride; wherein R₁ and R₂ are independently selected from the group consisting of alkyl, aryl, aralkyl, heterocycle and heteroaryl, each of which is optionally substituted; and X⁻ is a counterion.

In a further embodiment there is provided a method for the deoxofluorination of a compound comprising at least one functional group selected from the group consisting of —OH, —COOH and mixtures thereof, said method comprising contacting said compound with a disubstituted-amino difluorosulfinium salt represented by the formula:

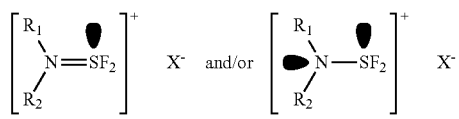

with a base; wherein R₁ and R₂ are independently selected from the group consisting of alkyl, aryl, aralkyl, heterocycle and heteroaryl, each of which is optionally substituted; and X⁻ is a counterion.

In one embodiment, the reaction is performed in the presence of an aprotic solvent selected in the group constituted by: halocarbons, ethers, esters, nitriles, aromatics and mixtures thereof. In a further embodiment, the reaction is conducted under anhydrous conditions and under inert atmosphere. The exogenous source of fluoride is preferably a complex consisting of hydrogen fluoride with an amine or an ammonium salt such as triethylamine trihydrogen fluoride, pyridinium poly(hydrogen fluoride) and tetrabutylammonium hydrogen difluoride. The base can be selected from the group consisting of DBU (1,8-diazabicyclo[5.4.0]undec-7-ene, DBN, (1,5-dazabicyclo[4.3.0]non-5-ene) DABCO (1,4diazabicyclo[2.2.2]octane, Hunig's base (ethyldiisopropylamine), tetramethyl guanidine, imidazole and alkali hydrides.

In the presence of exogenous promoters, the disubstituted-aminodifluorosulfinium salts have been found to be useful in a method for deoxofluorination of a compound comprising at least one functional group selected from the group consisting of —OH, ═O, —COOH.

The term deoxofluorination is known in the art and when applied in the present invention for compounds comprising at least one functional group selected from the group consisting of —OH, ═O and —COOH, means the replacement of a C—O bond by a C—F bond or a C═O double bond by two C—F bonds.

Compounds for use in deoxofluorination as used herein are not especially limited. Those compounds can be represented by the general formulae:

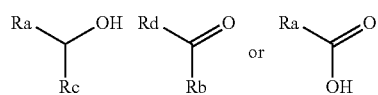

wherein Ra, Rb, Rc and Rd are each independently H or a group alkyl, alkene, alkyne, aryl, aralkyl, heterocycle and heteroaryl, each of which is optionally substituted
or Ra and Rc are attached together to form a cyclic alkyl or heterocycle each of which being optionally substituted;
or Rb and Rd are attached together to form a cyclic alkyl or heterocycle each of which being optionally substituted.

In

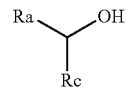

when Ra and Rc are attached together to form a heterocycle, it is also meant to include hemiacetal and hemiketals forms such as hemiacetals of saccharide derivatives.

Compounds described above when submitted to deoxofluorination conditions as described herein, will normally, having regard to the functional group(s) reactive present on the compound, give rise to fluorinated functional groups as follows or a combination thereof:

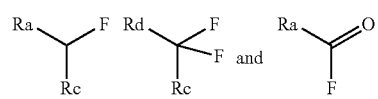

In accordance with one embodiment of the method of this disclosure for the deoxofluorination reaction, the reaction was performed in the presence of an exogenous fluoride source of ionic fluoride. In one embodiment, source of ionic fluoride is used in an amount of from catalytic to more than about stoichiometric. In one embodiment, more than stoichiometric amount is required such as 1.1 equivalents, 1.2 equivalents, 1.5 equivalents, 2 equivalents or more. Examples of exogenous fluoride source of ionic fluoride include a tertiary amine polyhydrogen fluoride or N-heteroaromatic amine polyhydrogen fluoride such as 3HF-Et$_3$N and 9HF-pyridine (Olah's reagent).

In one embodiment, the deoxofluorination reaction of a compound comprising at least one —OH group is conducted in the presence of an exogenous fluoride sources of ionic fluoride.

In one embodiment, the compound undergoing deoxofluorination reaction is other than an allylic alcohol and preferably other than an allylic alcohol containing prostaglandin derivatives.

In one embodiment, the deoxofluorination reaction of a compound comprising at least one =O group of an aldehyde is conducted in the presence of an exogenous fluoride sources of ionic fluoride.

In one embodiment, the deoxofluorination reaction of a compound comprising at least one =O group of a ketone is conducted in the presence of an exogenous fluoride sources of ionic fluoride.

In one embodiment, the deoxofluorination reaction of a compound comprising at least one —COOH group is conducted in the presence of an exogenous fluoride sources of ionic fluoride.

In accordance with one embodiment of the method of this disclosure for the deoxofluorination reaction, the reaction was performed in the presence of a base. In one embodiment, the base is used in an amount of from catalytic to more than about stoichiometric. In one embodiment, more than stoichiometric amount is required such as 1.1 equivalents, 1.2 equivalents, 1.5 equivalents, 2 equivalents or more. Examples of organic bases include 1,3-diazabicyclo[5.4.0]undecene (DBU), 1,3-diazabicyclo[4.3.0]nonene (DBN), as well as 1,1,3,3-tetramethylguanidine, disopropylethylamine (Hunig's base), 1,4-diazabicyclo[2,2,2]octane (DABCO), imidazole. Example of an inorganic base includes sodium hydride.

In one embodiment, the deoxofluorination reaction of a compound comprising at least one —OH group is conducted in the presence of an organic base.

In one embodiment, the deoxofluorination reaction of a compound comprising at least one —COOH group is conducted in the presence of an organic base.

EXAMPLES

The following examples are given only to illustrate the invention and should not be regarded as constituting any limitation of the scope of the invention in its broadest meaning.

Example 1

Preparation of Diethylaminodifluorosulfinium Tetrafluoroborate Salt

Method A

To an ice-cold solution of diethylaminosulfur trifluoride (8.2 mL, 62 mmol) in anhydrous diethyl ether (100 mL) is added, dropwise and under nitrogen, neat borontrifluoride etherate (6.6 mL, 62 mmol) over a period of 15 min, while keeping the reaction temperature below 5° C. The resulting suspension is stirred for an additional hour at the same temperature, then allowed to warm to room temperature and filtered under a blanket of nitrogen. The solid material is rinsed twice with diethyl ether (2×50 mL), then dried under vacuum to provide diethylaminodifluorosulfinium tetrafluoroborate (11.7 g, 82%) as a off-white hygroscopic solid; (1.60 g of the crude product is dissolved in 50 mL of warm 1,2-dichloroethane (DCE), rapidly cooled to r.t. over 5 min, then rapidly cooled to 0° C. to provide 1.34 g (84%) of off-white crystalline needles (Type I morphology); m.p. 72-76° C.; 5.0 g of the crude product is re-crystallized in 50 mL of boiling 1,2-dichloroethane with gradual cooling to r.t. over an hour to provide 4.6 g (92%) of white crystals flakes (Type II morphology); m.p. 83-84° C.); $^1$H NMR (CD$_3$CN, 300 MHz) δ 3.87 (m, 4H), 1.35 (t, J=7.2 Hz, 6H); $^{19}$F NMR (CD$_3$CN, 282 MHz) δ 12.9 (m, 2F), −151.1 (s, 4F); $^{13}$C NMR (CD$_3$CN, 75 MHz) δ 45.5, 12.6.

In an effort to simplify the process, and avoid the need to filter the crude diethylaminodifluorosulfinium tetrafluoroborate out of ether prior to the re-crystallization in 1,2-dichloroethane (DCE), we successfully performed the reaction directly in the latter solvent, then heated the mixture to ensure dissolution followed by cooling to crystallize the product. (Method B). Next, to further improve the process, and avoid the use of volatile diethyl ether, we substituted BF$_3$ etherate with BF$_3$ tetrahydrofuran complex (BF$_3$-THF). In this context, the salt slowly crystallized out of the reaction mixture and the recrystallization of the crude reaction mixture was not performed. (Method C).

Example 2

Preparation of Diethylaminodifluorosulfinium Tetrafluoroborate Salt

Method B

To an solution of diethylaminosulfur trifluoride (8.2 mL, 62 mmol) in anhydrous 1,2-dichloroethane (150 mL) at room temperature is added, dropwise and under nitrogen, neat borontrifluoride etherate (6.6 mL, 62 mmol) over a period of 15 min, while keeping the reaction temperature below 30° C. The resulting suspension is heated to reflux, then gradually cooled to room temperature (solids appeared at 60° C. when seeded). The suspension is stirred an additional 2 hours, then filtered under a blanket of nitrogen. The solid material is rinsed twice with 1,2-dichloroethane (2×25 mL), then dried under vacuum to provide diethylaminodifluorosulfinium tetrafluoroborate (12.6 g, 89%) as colorless flakes (Type III morphology); m.p. 83-84° C.

Example 3

Preparation of Diethylaminodifluorosulfinium Tetrafluoroborate Salt

Method C

To a solution of diethylaminosulfur trifluoride (8.2 mL, 62 mmol) in anhydrous 1,2-dichloroethane (150 mL) at room temperature is added, dropwise and under nitrogen, neat borontrifluoride tetrahydrofuran complex (6.8 mL, 62 mmol) over a period of 45 min, while keeping the reaction temperature below 30° C. Crystallization occurs after approximately 4 mL of BF$_3$-THF is added. The suspension is stirred an additional 30 min, then filtered under a blanket of nitrogen. The solid material is rinsed twice with diethyl ether (2×50 mL), then dried under vacuum to provide diethylaminodifluorosulfinium tetrafluoroborate (12.1 g, 85%) as colorless prisms (Type IV morphology); m.p. 83-85° C.

All the aforementioned preparative methods used commercially available diethylaminosulfur trifluoride (DAST). The latter reagent is a know explosive and purification of this unstable liquid requires an hazardous distillation. This laborious means of purification requires extensive safety measures and is a major cost-contributor to this relatively expensive reagent. Instead of DAST, we found that diethylaminodifluorosulfinium tetrafluoroborate could be prepared in a one-pot process using N,N-diethyltrimethylsilylamine as a relatively inexpensive and stable starting material (Method D). Although DAST is an intermediate in this preparative method, the distillation of DAST was not required as we surprisingly found that the by-products generated in the process did not interfere with the diethylaminodifluorosulfinium tetrafluoroborate salt-formation. This novel preparative method therefore allows the manufacture of the latter in a safer and cost efficient manner. This encompasses other potential methods for producing crude and undistilled disubstituted aminosulfur trifluoride using alternative reagents (such as a secondary amine and a base) and/or processing techniques (such as a continuous flow process).

Example 4

Preparation of Diethylaminodifluorosulfinium Tetrafluoroborate Salt

Method D

To a 5 L flange necked flask fitted with magnetic stirrer, temp probe, bubbler and nitrogen inlet was added dichloromethane (150 mL) and then cooled to −78° C. Sulfur tetrafluoride (70 g, 0.65 mol) was sub-surfaced while keeping the temperature below −65° C. To the resulting solution was added dropwise a solution of diethylaminotrimethylsilane (90 g, 0.62 mol) in dichloromethane (42 mL) while keeping the temperature below −60° C. The resulting solution was allowed to slowly warm to room temperature and stirred overnight. To the resulting solution was added dichloromethane (558 mL) followed by boron trifluoride tetrahydrofuran complex (68 mL, 0.61 mol) dropwise over 30 min keeping the temperature between 15 and 25° C. The suspension was stirred an additional 60 min, then filtered under a blanket of nitrogen. The solid material was rinsed with diethyl ether (3×150 mL), then dried under vacuum to provide 1 (126 g, 89%) as off-white crystal plates (Type V morphology): mp 83-85° C. In a trial experiment, diethylaminodifluorosulfinium tetrafluoroborate (2.00 g) was melted with heating, then 1,2-dichloroethane was added and the resulting mixture was further heated to reflux to obtain a bi-phasic liquid mixture. The latter was allowed to cool-down to room temperature and the resulting solid material was isolated by filtration and dried under vacuum to provide 1 (1.98 g, 99%) as off-white crystal cubes (Type VI morphology): mp 83-85° C.

Characterization:

Applicant has observed that diethylaminodifluorosulfinium tetrafluoroborate salt crystallizes directly out of solution upon the reaction of DAST and $BF_3$ etherate in diethyl ether. The salt is very moisture sensitive but filterable. In an effort to obtain a less hygroscopic solid, the forgoing salt was initially re-crystallized in 1,2-dichloroethane, which upon rapid cooling led to needles melting at 72-76° C., consistent with Markovskii's published results (Zh. Org. Khim. 1977, 13, 1116). A second crystallization trial in reluxing 1,2-dichloroethane with slower cooling did not lead to same morphology, even when seeded with aforementioned needles. However, a denser and cleaner product with a higher melting point of 83-84° C. is obtained (Example 1; type II morphology). Surprisingly, in all of the subsequent methods employed to produce diethylaminodifluorosulfinium tetrafluoroborate salts (example 2-4), the observed melting points were all in the range of 83-85° C., but the overall physical appearance of the crystals were all different from each other.

Powder x-ray diffraction (XRD) data of the various crystals (morphologies type 1-VI) shown in FIGS. 1a-1f, is acquired using an X-ray powder diffractometer (Bruker-axs, model D8 advance) having the following parameters: voltage 40 kV, current 40.0 mA, scan range (2θ) 5 to 35°, scan step size 0.01°, total scan time 33 minutes, VANTEC detector, and antiscattering slit 1 mm and provided the listing of Angle 2-theta, d-lines and Relative Intensity at about the values provided in table 1.

TABLE 1

| Type I | | | Type II | | | Type III | | | Type IV | | | Type V | | | Type VI | | |
|---|---|---|---|---|---|---|---|---|---|---|---|---|---|---|---|---|---|
| d | 2-theta | % | d | 2-theta | % | d | 2-theta | % | d | 2-theta | % | d | 2-theta | % | d | 2-theta | % |
| | | | | | | 19.93 | 4.4 | 5.8 | | | | | | | 19.97 | 4.4 | 2.3 |
| | | | | | | | | | 17.37 | 5.1 | 0.6 | | | | | | |
| | | | | | | 11.49 | 7.7 | 2.4 | | | | 11.51 | 7.7 | 1.1 | | | |
| | | | 7.99 | 11.1 | 15.1 | 7.97 | 11.1 | 7.2 | 8 | 11 | 1.5 | 8 | 11.1 | 1.1 | 7.97 | 11.1 | 6.2 |
| 7.24 | 12.2 | 12.9 | 7.26 | 12.2 | 100 | 7.24 | 12.2 | 8.6 | 7.26 | 12.2 | 100 | 7.26 | 12.2 | 4.4 | 7.23 | 12.2 | 100 |
| 6.69 | 13.2 | 100 | 6.71 | 13.2 | 68 | 6.69 | 13.2 | 40.5 | 6.71 | 13.2 | 50.2 | 6.71 | 13.2 | 100 | 6.68 | 13.2 | 21 |
| | | | 6.04 | 14.6 | 4.8 | | | | | | | | | | | | |
| | | | 5.61 | 15.8 | 52.7 | 5.6 | 15.8 | 12.4 | 5.61 | 15.8 | 1.5 | 5.61 | 15.8 | 3.8 | 5.6 | 15.8 | 4.1 |
| | | | 5.46 | 16.2 | 4.3 | | | | | | | | | | 5.44 | 16.3 | 1 |
| 5.17 | 17.1 | 0.6 | 5.17 | 17.1 | 52.5 | 5.16 | 17.2 | 7.4 | 5.17 | 17.1 | 1.5 | 5.18 | 17.1 | 0.6 | 5.16 | 17.2 | 9.6 |
| | | | 4.95 | 17.9 | 18.6 | 4.94 | 17.9 | 7.8 | | | | 4.95 | 17.9 | 1.5 | 4.95 | 17.9 | 4.3 |
| | | | 4.87 | 18.2 | 18.4 | 4.87 | 18.2 | 100 | 4.87 | 18.2 | 28.3 | 4.87 | 18.2 | 44.9 | 4.87 | 18.2 | 1 |
| | | | 4.45 | 19.9 | 19.4 | 4.45 | 20 | 14.2 | 4.45 | 19.9 | 0.7 | 4.45 | 19.9 | 4 | 4.44 | 20 | 1.1 |
| | | | 4.36 | 20.4 | 19.2 | | | | | | | | | | 4.35 | 20.4 | 5.4 |
| 4.3 | 20.6 | 4.2 | 4.32 | 20.5 | 59.7 | 4.31 | 20.6 | 12.9 | 4.31 | 20.6 | 4.6 | 4.31 | 20.6 | 3.8 | 4.31 | 20.6 | 7.3 |
| | | | 4.02 | 22.1 | 17.7 | 4.01 | 22.1 | 4.9 | | | | 4.01 | 22.2 | 0.9 | 4 | 22.2 | 4.4 |
| | | | | | | | | | | | | 3.97 | 22.4 | 0.4 | | | |
| 3.79 | 23.4 | 1.3 | 3.8 | 23.4 | 6.5 | 3.79 | 23.4 | 5.1 | 3.8 | 23.4 | 1.7 | 3.8 | 23.4 | 1.8 | 3.79 | 23.5 | 3.3 |
| | | | | | | 3.69 | 24.1 | 1.2 | | | | | | | | | |
| 3.63 | 24.5 | 3.6 | 3.63 | 24.5 | 76.1 | 3.63 | 24.5 | 11.5 | 3.64 | 24.5 | 23.1 | 3.63 | 24.5 | 2.9 | 3.63 | 24.5 | 92.1 |
| 3.51 | 25.3 | 1.7 | 3.51 | 25.3 | 7 | 3.51 | 25.3 | 5.8 | 3.51 | 25.3 | 2 | 3.52 | 25.3 | 2.5 | 3.51 | 25.4 | 2.2 |
| | | | 3.47 | 25.6 | 7.3 | 3.46 | 25.7 | 3.6 | | | | 3.46 | 25.7 | 0.7 | 3.48 | 25.6 | 1.9 |
| | | | 3.41 | 26.1 | 10.7 | | | | | | | | | | 3.41 | 26.1 | 0.9 |
| | | | 3.39 | 26.3 | 9.3 | 3.39 | 26.3 | 2.7 | | | | 3.36 | 26.5 | 1 | 3.39 | 26.3 | 1.1 |

TABLE 1-continued

| Type I | | | Type II | | | Type III | | | Type IV | | | Type V | | | Type VI | | |
|---|---|---|---|---|---|---|---|---|---|---|---|---|---|---|---|---|---|
| d | 2-theta | % | d | 2-theta | % | d | 2-theta | % | d | 2-theta | % | d | 2-theta | % | d | 2-theta | % |
| 3.35 | 26.6 | 0.7 | | | | | | | | | | | | | | | |
| 3.3 | 27 | 0.2 | | | | | | | | | | | | | | | |
| 3.27 | 27.3 | 0.3 | 3.27 | 27.2 | 56 | 3.27 | 27.2 | 19.1 | 3.27 | 27.2 | 7.6 | 3.28 | 27.2 | 6.3 | 3.26 | 27.4 | 2.6 |
| | | | 3.21 | 27.8 | 9.4 | | | | | | | | | | 3.21 | 27.8 | 2.3 |
| | | | 3.14 | 28.4 | 26.8 | 3.13 | 28.4 | 7.6 | | | | 3.14 | 28.4 | 1.5 | | | |

The aforementioned XRD confirmed the generation of distinctly different morphologies. Whereas Markovskii reported obtaining needles (referred to as type I morphology and presented in FIG. 1a) with a m.p. of 74-76° C., the new morphologies all have higher melting points in the range of 83-85° C. Beyond the physical appearance, the applicants have observed that some morphologies exhibited better handling properties and are less hygroscopic than others. To assess the relative stabilities of morphologies type II, IV, V and VI towards atmospheric moisture, 250 mg of these forms were evenly dispersed on a 25 square centimeter glass surface and exposed to a relative humidity of 23% at 20° C. After 30 minutes, samples were analysed by NMR to measure the amount of hydrolysis. Type VI morphology was found surprisingly stable to atmospheric moisture since only 1.14% hydrolysed under these conditions, whereas type II, IV and V were hydrolysed in 2.97%, 10.03% and 16.29%. Moreover, type VI can be easily manipulated and storage stable.

Example 5

Recrystallisation of Diethylaminodifluorosulfinium Tetrafluoroborate to Type VI Polymorph A suspension of diethylaminodifluorosulfinium tetrafluoroborate (50.0 g) in 1,2-dichloroethane (250 mL) was heated to reflux until the salt is completely melted. The resulting by-phasic liquid mixture was allowed to cool-down to 65° C., at which point type VI seeds (5.0 g) were added at once. The reaction mixture was then allowed to cool to room temperature and stirred 2.5 h. The resulting solid material was isolated by filtration and dried under vacuum to provide diethylaminodifluorosulfinium tetrafluoroborate (54.1 g, 98%) as off-white crystal cubes (Type VI morphology): mp 83-85° C.

Example 6

Preparation of Morpholinodifluorosulfinium Tetrafluoroborate Salt

Method A

To an ice-cold solution of morpholinosulfur trifluoride (4.9 mL, 40 mmol) in anhydrous diethyl ether (100 mL) is added, dropwise and under nitrogen, a solution of borontrifluoride etherate (4.2 mL, 40 mmol) in anhydrous diethyl ether (25 mL) over a period of 60 min, while keeping the reaction temperature below 5° C. The resulting suspension is stirred for an additional hour at the same temperature, then allowed to warm to room temperature and filtered under a blanket of nitrogen. The solid material is rinsed twice with diethyl ether (2×50 mL), then dried under vacuum to provide morpholinodifluorosulfinium tetrafluoroborate (7.3 g, 75%) as a white solid; m.p. 122-125° C.; $^1$H NMR (CD$_3$CN, 300 MHz) δ 3.90-3.85 (m, 8H); $^{19}$F NMR (CD$_3$CN, 282 MHz) δ 10.2 (s, 2F), −151.3 (s, 4F); $^{13}$C NMR (CD$_3$CN, 75 MHz) δ 65.7, 48.3 (br).

Example 7

Preparation of Morpholinodifluorosulfinium Tetrafluoroborate Salt

Method B

To a 10 L flange necked flask fitted with magnetic stirrer, temp probe, bubbler and nitrogen inlet was added dichloromethane (750 mL) and then cooled to −78° C. Sulfur tetrafluoride (321 g, 2.97 mol) was sub-surfaced while keeping the temperature below −65° C. To the resulting solution was added dropwise a solution of N-trimethylsilylmorpholine (455 g, 2.86 mol) in dichloromethane (210 mL) while keeping the temperature below −60° C. The resulting solution was allowed to slowly warm to room temperature and stirred overnight. To the resulting solution was added dichloromethane (2.79 L) followed by boron trifluoride tetrahydrofuran complex (315 mL, 2.85 mol) dropwise over 180 min keeping the temperature below 25° C. The suspension was stirred an additional 60 min, then filtered under a blanket of nitrogen. The solid material was rinsed with diethyl ether (3×750 mL), then dried under vacuum to provide 1 (635 g, 92%) as off-white crystals: mp 124-127° C.

Characterization:

The morpholinodifluorosulfinium tetrafluoroborate salt can be prepared using commercially available morpholinosulfur trifluoride (MOST) as starting material (Method A). However, the latter reagent is a know explosive and purification of this unstable liquid requires an hazardous distillation. This laborious means of purification requires extensive safety measures and is a major cost-contributor to this relatively expensive reagent. Instead of using MOST, we found that morpholinodifluorosulfinium tetrafluoroborate could be prepared in a one-pot process using N-trimethylsilylmorpholine as a relatively inexpensive and stable starting material (Method B). Although MOST is an intermediate in this preparative method, the distillation of MOST was not required as we surprisingly found that the by-products generated in the process did not interfere with the diethylamino-difluorosulfinium tetrafluoroborate salt-formation. This novel preparative method therefore allows the manufacture of the latter in a safer and cost efficient manner.

Unexpectedly, the two methods used to prepare morpholinodifluorosulfinium tetrafluoroborate provided crystalline material with significantly higher melting points (122 to 127° C.) than the one reported by Markovskii (104-106° C.). This constitutes a clear indication of a novel polymorphic form, and the material was found easy to handle and storage stable. Powder x-ray diffraction (XRD) data of the new polymorphic form, is acquired using an X-ray powder diffractometer (Bruker-axs, model D8 advance) having the following parameters: voltage 40 kV, current 40.0 mA, scan range (2θ) 5 to 35°, scan step size 0.01°, total scan time 33 minutes, VANTEC detector, and antiscattering slit 1 mm and provided the listing of Angle 2-theta, d-lines and Relative Intensity at about the values provided in the table 2.

TABLE 2

| Angle 2-theta (°) | d (angstrom) | Relative Intensity (%) |
|---|---|---|
| 4.43 | 19.91 | 19.4 |
| 13.16 | 6.72 | 56.4 |
| 14.00 | 6.32 | 58.3 |
| 14.31 | 6.18 | 6.5 |
| 15.79 | 5.61 | 42.4 |
| 17.36 | 5.10 | 10.3 |
| 18.39 | 4.82 | 100 |
| 19.51 | 4.55 | 10.8 |
| 21.75 | 4.08 | 92.6 |
| 23.33 | 3.81 | 11.3 |
| 23.59 | 3.77 | 96.6 |
| 24.69 | 3.60 | 2.0 |
| 25.42 | 3.50 | 12.8 |
| 26.43 | 3.37 | 7.8 |
| 26.65 | 3.34 | 6.1 |
| 27.93 | 3.19 | 6.1 |
| 28.59 | 3.12 | 12.6 |
| 28.83 | 3.09 | 7.7 |
| 29.46 | 3.03 | 4.6 |
| 29.88 | 2.99 | 3.4 |

Example 8

Preparation of bis(2-methoxyethyl)aminodifluorosulfinium Tetrafluoroborate Salt

To an ice-cold solution of bis(2-methoxyethyl)aminosulfur trifluoride (16.7 mL, 90.4 mmol) in anhydrous diethyl ether (200 mL) is added, dropwise and under nitrogen, a solution of borontrifluoride etherate (9.5 mL, 90.4 mmol) in anhydrous diethyl ether (50 mL) over a period of 60 min, while keeping the reaction temperature below 5° C. The resulting suspension is stirred for an additional hour at the same temperature, then allowed to warm to room temperature and filtered under a blanket of nitrogen. The solid material is rinsed twice with diethyl ether (2×100 mL), then dried under vacuum to provide bis(2-methoxyethyl)aminodifluorosulfinium tetrafluoroborate (20.36 g, 78%) as an off-white hygroscopic solid; m.p. 35-38° C.; $^1$H NMR (CD$_3$CN) 4.07 (m, 4H), 3.60 (m, 4H), 3.43 (s, 6H); $^{19}$F NMR (CD$_3$CN) 10.22 (s, 2F), −151.47 (s, 4F); $^{13}$C NMR (CD$_3$CN) 67.08, 58.92, 51.53.

Example 9

Preparation of Dimethylaminodifluorosulfinium Tetrafluoroborate Salt

To an ice-cold solution of dimethylaminosulfur trifluoride (5.0 g, 38 mmol) in anhydrous diethyl ether (50 mL) is added, dropwise and under nitrogen, neat borontrifluoride etherate (4.0 mL, 38 mmol) over a period of 15 min, while keeping the reaction temperature below 5° C. The resulting suspension is stirred for an additional hour at the same temperature, then allowed to warm to room temperature and filtered under a blanket of nitrogen. The solid material is rinsed twice with diethyl ether (2×25 mL), then dried under vacuum to provide dimethylaminodifluorosulfinium tetrafluoroborate (5.17 g, 68%) as a white solid; m.p. 159-162° C.; $^1$H NMR (CD$_3$CN) 3.41 (t, J=7.5 Hz, 6H); $^{19}$F NMR (CD$_3$CN) 12.14 (m, J=7.9 Hz, 2F), −151.54 (m, 4F); $^{13}$C NMR (CD$_3$CN) 38.78 (br).

Example 10

Preparation of Pyrrolidinodifluorosulfinium Tetrafluoroborate Salt

Step 1—To an ice-cold solution of pyrrolidine (167 ml, 2.00 mol) in diethyl ether (500 ml) was added a solution of chlorotrimethylsilane (127 ml, 1.00 mol) in diethyl ether (100 ml) over 1 hour. The solid was removed by filtration and washed with diethyl ether (100 ml). The filtrates were concentrated in vacuo then distilled at atmospheric pressure to give N-trimethylsilylpyrrolidine (104 g, 73%) as a colorless liquid: b.p. 139-140° C.; $^1$H NMR (CDCl$_3$) 0.09 (s, 9H), 1.74 (m, 4H), 2.91 (m, 4H); $^{13}$C NMR (CDCl$_3$) 3.50, 28.26, 48.33

Step 2—To a 5 L flange necked flask fitted with magnetic stirrer, temp probe, bubbler and nitrogen inlet was added dichloromethane (150 mL) and then cooled to −78° C. Sulfur tetrafluoride (70.6 g, 0.65 mol) was sub-surfaced while keeping the temperature below −65° C. To the resulting solution was added dropwise a solution of N-trimethylsilylpyrrolidine (90 g, 0.62 mol) in dichloromethane (42 mL) while keeping the temperature below −60° C. The resulting solution was allowed to slowly warm to room temperature and stirred overnight. To the resulting solution was added dichloromethane (558 mL) followed by boron trifluoride tetrahydrofuran complex (69 mL, 0.63 mol) dropwise over 60 min keeping the temperature below 25° C. The suspension was stirred an additional 60 min, then filtered under a blanket of nitrogen. The solid material was rinsed with diethyl ether (3×150 mL), then dried under vacuum to provide pyrrolidinodifluorosulfinium tetrafluoroborate (121 g, 85%) as beige crystals: mp 105-113° C.: $^1$H NMR (CD$_3$CN) 4.10-3.98 (m, 4H), 2.19-2.12 (m, 4H); $^{19}$F NMR (CD$_3$CN) 12.09 (q, J=7.6 Hz), −151.26 (s); $^{13}$C NMR (CD$_3$CN) 53.12, 25.86.

Example 11

Preparation of N-Methyl-N-Phenylaminodifluorosulfinium Tetrafluoroborate Salt

Step 1—To a stirring solution of N-methylaniline (80 g, 0.75 mol) in diethyl ether (600 ml) cooled at −78° C. was added n-butyl lithium (2.4 M in hexanes, 342 ml, 0.82 mol) keeping the temperature below −60° C. The resulting slurry was stirred for 1 hour then chlorotrimethylsilane (114 ml, 0.90 mol) was added while keeping the temperature below −70° C. The reaction was allowed to warm to room temperature overnight then filtered to remove the precipitated white solid. The filtrates were concentrated in vacuo then distilled under high-vac to yield the N-trimethylsilyl-N-methylaniline (126 g, 94%) as a colorless/straw colored liquid: b.p. 48° C./0.6 mmHg; $^1$H NMR (CDCl$_3$) 0.33 (s, 9H), 2.95 (s, 3H), 6.85 (t, 1H, 7 Hz), 6.94 (d, 2H, 8 Hz), 7.27 (t, 2H, 9 Hz).

Step 2—To a 5 L flange necked flask fitted with magnetic stirrer, temp probe, bubbler and nitrogen inlet was added dichloromethane (150 mL) and then cooled to −78° C. Sulfur tetrafluoride (57.1 g, 0.53 mol) was sub-surfaced while keeping the temperature below −65° C. To the resulting solution was added dropwise a solution of N-trimethylsilyl-N-methylaniline (91.2 g, 0.51 mol) in dichloromethane (42 mL) while keeping the temperature below −70° C. The resulting solution was allowed to slowly warm to room temperature and stirred overnight. To the resulting solution was added dichloromethane (558 mL) followed by boron trifluoride tetrahydrofuran complex (56 mL, 0.51 mol) dropwise over 70 min keeping the temperature below 25° C. The suspension was stirred an additional 60 min, then filtered under a blanket of nitrogen. The solid material was rinsed with diethyl ether (3×150 mL), then dried under vacuum to provide N-methyl-N-phenylaminodifluorosulfinium tetrafluoroborate (124 g, 93%) as dark-grey crystals: mp 144-150° C.; $^1$H NMR (CD$_3$CN) 7.74-7.49 (m, 5H), 3.92-3.75 (m, 3H); $^{19}$F NMR (CD$_3$CN) 14.33 (s), −150.41 (s); $^{13}$C NMR (CD3CN) 132.82, 131.46, 128.02, 122.74, 43.82.

Example 12

Preparation of N-Benzyl-N-Methylaminodifluorosulfinium Tetrafluoroborate Salt Step 1—To a stirring solution of N-methylbenzylamine (100 ml, 93.9 g, 0.77 mol) in diethyl ether (500 ml) cooled at −78° C. was added n-butyl lithium (2.4 M in hexanes, 355 ml, 0.85 mol) keeping the temperature below −60° C. The resulting slurry was stirred for 1 hour then chlorotrimethylsilane (118 ml, 0.93 mol) was added while keeping the temperature below −70° C. The reaction was allowed to warm to room temperature overnight then filtered to remove the precipitated white solid. The filtrates were concentrated in vacuo then distilled under high-vacuum to yield the N-trimethylsilyl-N-methylbenzylamine (102 g, 94%) as a colorless liquid: b.p. 54° C./0.5 mmHg; $^1$H NMR (CDCl$_3$) 0.19 (s, 9H), 2.37 (s, 3H), 3.90 (2, 2H) 7.22-7.39 (m, 5H)

Step 2—To a 5 L flange necked flask fitted with magnetic stirrer, temp probe, bubbler and nitrogen inlet was added dichloromethane (150 mL) and then cooled to −78° C. Sulfur tetrafluoride (53.7 g, 0.50 mmol) was sub-surfaced while keeping the temperature below −65° C. To the resulting solution was added dropwise a solution of N-trimethylsilyl-N-methylbenzylamine (92.4 g, 0.48 mol) in dichloromethane (42 mL) while keeping the temperature below −70° C. The resulting solution was allowed to slowly warm to room temperature and stirred overnight. To the resulting solution was added dichloromethane (558 mL) followed by boron trifluoride tetrahydrofuran complex (52.7 mL, 0.48 mol) dropwise over 70 min keeping the temperature below 25° C. The solution was cooled to −78° C. and a solid precipitated and then filtered under a blanket of nitrogen. The solid material was rinsed with diethyl ether (3×150 mL), then dried under vacuum to provide N-benzyl-N-methylaminodifluorosulfinium tetrafluoroborate (93 g, 73%) as beige crystals: mp 59-62° C.: $^1$H NMR (CD$_3$CN) 7.57-7.40 (brm) 5.07-4.94 (brm), 3.31-3.16 (brm); $^{19}$F NMR (CD$_3$CN) 14.13 (s)-150.85 (s); $^{13}$C NMR (CD$_3$CN) 130.46, 130.32, 129.92, 55.07, 35.87.

Example 13

Preparation of N-methyl-N-(2-pyridyl)aminodifluorosulfinium Tetrafluoroborate Salt Step 1—To a stirring solution of 2-methylaminopyridine (19.5 g, 0.18 mol) in diethyl ether (120 ml) cooled at −78° C. was added n-butyl lithium (2.4 M in hexanes, 85 ml, 0.20 mol) keeping the temperature below −70° C. The resulting slurry was stirred for 1 hour then chlorotrimethylsilane (28.2 ml, 0.22 mol) was added while keeping the temperature below −70° C. The reaction was allowed to warm to room temperature overnight then filtered to remove the precipitated white solid. The filtrates were concentrated in vacuo then distilled under high-vac to yield the N-trimethylsilyl-N-methyl-2-aminopyridine (31.9 g, 96%) as a colourless liquid: b.p. 50° C./0.5 mmHg; $^1$H NMR (CDCl$^3$) 0.33 (s, 9H), 2.86 (s, 3H), 6.51 (d, 1H, 8 Hz), 6.62 (m, 1H), 7.49 (m, 1H), 8.12 (m, 1H); $^{13}$C NMR (CDCl$^3$) 0.00, 30.91, 105.03, 111.38, 136.05, 145.94, 160.74

Step 2—To a 5 L flange necked flask fitted with magnetic stirrer, temp probe, bubbler and nitrogen inlet was added dichloromethane (150 mL) and then cooled to −78° C. Sulfur tetrafluoride (23.7 g, 0.22 mol) was sub-surfaced while keeping the temperature below −70° C. To the resulting solution was added dropwise a solution of N-trimethylsilyl-N-methyl-2-aminopyridine (38.0 g, 0.21 mol) in dichloromethane (42 mL) while keeping the temperature below −70° C. The resulting solution was allowed to slowly warm to room temperature and stirred overnight. To the resulting solution was added dichloromethane (500 mL) followed by boron trifluoride tetrahydrofuran complex (23.3 mL, 0.21 mol) dropwise over 35 min keeping the temperature below 21° C. The suspension was stirred an additional 60 min, then filtered under a blanket of nitrogen. The solid material was rinsed with diethyl ether (3×150 mL), then dried under vacuum to provide N-methyl-N-(2-pyridyl)aminodifluorosulfinium tetrafluoroborate (43.6 g, 78%) as white crystals: m.p. 80-86° C.; $^1$H NMR (CD$_3$CN) 8.40 (d, J=4.6 Hz, 1H), 8.21 (t, J=8.0 Hz, 1H), 7.59 (dd, J=7.6, 5.6 Hz, 1H), 7.44 (d, J=8.3 Hz, 1H), 3.75 (s, 3H); $^{19}$F NMR (CD$_3$CN)-9.11 (s), −151.23 (s); $^{13}$C NMR (CD$_3$CN) 148.70, 146.98, 143.76, 124.94, 112.12, 33.80.

Surprisingly, applicant has observed that DAST reacts exothermically with a strong Bronsted acid such as tetrafluoroboric acid to provide dialkylaminodifluorosulfinium tetrafluoroborate and HF as described below. This finding constitutes a novel method for the preparation of dialkylaminodifluorosulfinium salts. Insofar, all the previously reported dialkylaminodifluorosulfinium salts were prepared via fluorination of BF$_3$, PF$_5$, AsF$_5$, SeF$_4$, SbF$_5$, and the types of salts were limited to the corresponding counteranions. Now, other types of counterions are accessible via this novel Bronsted acid exchange method. In another example described below, diethylaminodifluorosulfinium trifluoromethanesulfonate salt can be readily prepared by contacting DAST with triflic acid. Applicant has also found that triflic anhydride could be used instead of triflic acid to produce triflate salts.

Example 14

Preparation of Diethylaminodifluorosulfinium Tetrafluoroborate Salt

Method E

To a solution of diethylaminosulfur trifluoride (4.1 mL, 31 mmol) in anhydrous diethyl ether (50 mL) at room temperature is added, dropwise and under nitrogen, neat tetrafluoroboric acid diethyl ether complex (4.2 mL, 31 mmol) over a period of 30 min, while keeping the reaction temperature below 30° C. Precipitation occurs immediately upon the start of the addition. The resulting suspension is stirred an additional 20 min, then filtered under a blanket of nitrogen. The solid material is rinsed twice with diethyl ether (2×25 mL), then dried under vacuum to provide diethylaminodifluorosulfinium tetrafluoroborate (6.7 g, 96%) as off-white solid; m.p. 77-84° C.

Example 15

Preparation of Diethylaminodifluorosulfinium Tetrafluoroborate Salt

Method F

To a 3 L flange necked flask fitted with magnetic stirrer, temp probe, bubbler and nitrogen inlet was added dichloromethane (150 mL) and then cooled to −78° C. Sulfur tetrafluoride (69.7 g, 0.65 mmol) was sub-surfaced while keeping the temperature below −65° C. To the resulting solution was added dropwise a solution of diethylaminotrimethylsilane (90.1 g, 0.62 mol) in dichloromethane (42 mL) while keeping the temperature below −70° C. The resulting solution was allowed to slowly warm to room temperature and stirred overnight. To the resulting solution was added dichloromethane (558 mL) followed by tetrafluoroboric acid diethyl ether complex (85 ml, 0.62 mol) dropwise over 65 minutes keeping the temperature between 16 and 19° C. The suspension was stirred an additional 60 min, then filtered under a blanket of nitrogen. The solid material was rinsed with diethyl ether (3×150 mL), then dried under vacuum to provide diethylaminodifluorosulfinium tetrafluoroborate (76 g, 54%) as very pale brown crystals: m.p. 84-86° C.

Example 16

Preparation of Diethylaminodifluorosulfinium Trifluoromethanesulfonate Salt

Method A

Using Trifluoromethanesulfonic Acid

To an ice-cold solution of diethylaminosulfur trifluoride (2.45 mL, 18.6 mmol) in anhydrous diethyl ether (30 mL) is added, dropwise and under nitrogen, neat trifluoromethanesulfonic acid (1.65 mL, 18.6 mmol) over a period of 5 min. The resulting suspension is stirred for an additional 30 min at the same temperature, then filtered under a blanket of nitrogen. The solid material is rinsed twice with diethyl ether (2×20 mL), then dried under vacuum to provide diethylaminodifluorosulfinium trifluoromethanesulfonate (4.4 g, 81%) as a white solid; m.p. 97-101° C.); $^1$H NMR (CD$_3$CN, 300 MHz) δ 3.91 (m, 4H), 1.38 (t, J=7.0 Hz, 6H); $^{19}$F NMR (CD$_3$CN, 282 MHz) δ 12.5 (s, 2F), −79.8 (s, 3F); $^{13}$C NMR (CD$_3$CN, 75 MHz) δ 121.4 (q, J=320.0 Hz), 48.3 (br), 12.4.

Example 17

Preparation of Diethylaminodifluorosulfinium Trifluoromethanesulfonate Salt

Method B

From Triflic Anhydride

To an ice-cold solution of diethylaminosulfur trifluoride (1.64 mL, 12.4 mmol) in anhydrous dichloromethane (16 mL) is added, dropwise and under nitrogen, neat trifluoromethanesulfonic anhydride (2.09 mL, 12.4 mmol) over a period of 10 min. The resulting suspension is filtered under a blanket of nitrogen. The solid material is rinsed twice with diethyl ether (2×10 mL), then dried under vacuum to provide diethylaminodifluorosulfinium trifluoromethanesulfonate (3.15 g, 74%) as a white solid; m.p. 109-111° C.).

Example 18

Preparation of Morpholinodifluorosulfinium Trifluoromethanesulfonate Salt

To a solution of morpholinosulfur trifluoride (2.1 mL, 17.1 mmol) in anhydrous diethyl ether (25 mL) at room temperature is added, dropwise and under nitrogen, a solution of trifluoromethanesulfonic acid (1.5 mL, 17.1 mmol) in diethyl ether (10 mL) over a period of 30 min. The resulting suspension is stirred for an additional 90 min at the same temperature, then filtered under a blanket of nitrogen. The solid material is rinsed twice with diethyl ether (2×20 mL), then dried under vacuum to provide diethylaminodifluorosulfinium trifluoromethanesulfonate (4.24 g, 81%) as a white solid; m.p. 85-87° C.); $^1$H NMR (CD$_3$CN); $^{19}$F NMR (CD$_3$CN). $^1$H NMR (CD$_3$CN, 300 MHz) δ 4.11-3.98 (m, 8H) $^{19}$F NMR (CD$_3$CN, 282 MHz) δ 9.9 (s, 2F), −79.6 (s, 3F); $^{13}$C NMR (CD$_3$CN, 75 MHz) δ 123.5 (d, J=320.8 Hz), 65.7, 48.2 (br).

Safety Studies:

Due to the known explosive nature of parent dialkylaminosulfur trifluorides, the thermal stability of the various disubstituted aminodifluorosulfinium salts was assessed by DSC (differential scanning calorimetry). In Lal's account, DAST reportedly decomposes at 140° C., releasing 1700 J/g whereas Deoxo-Fluor decomposes at 140° C. with 1100 J/g of energy. Since reported DSC values are variable, DAST and Deoxo-Fluor were re-tested in the same instrument used to test the various disubstituted aminodifluorosulfinium salts. Thus, DAST exhibited a very sharp peak at 155° C. and a release of 1641 J/g. In comparison, diethylaminodifluorosilfinium tetrafluoroborate's Tmax was 205° C. with an exothermic heat of decomposition of 1260 J/g. In general, a higher decomposition temperature and a lower exothermic heat generated during decomposition is indicative of a more stable compound and provides greater safety. Morpholinodifluorosulfinium tetrafluoroborate was even more stable with a Tmax of 243° C. while releasing only 773 J/g. These results favorably compare to Deoxo-Fluor which released 1031 J/g at a $T_{max}$ of 158° C. Moreover, isothermal DSC of both XtalFluor-E and XtalFluor-M set at 90° C. showed no observable degradation in the timeframe tested, i.e. 5000 minutes. At the same temperature, DAST and Deoxo-Fluor were reported to degrade within 300 and 1800 minutes respectively. The DSC values of various salts are summarized in table 3.

TABLE 3

| Experiment | Compound | Tmax (° C.) | −ΔH(J/g) |
|---|---|---|---|
| 19 | Et$_2$N—SF$_3$ | 155 | 1641 |
| 20 | (MeOCH$_2$CH$_2$)$_2$N—SF$_3$ | 158 | 1031 |

TABLE 3-continued

| Experiment | Compound | Tmax (° C.) | −ΔH(J/g) |
|---|---|---|---|
| 21 | Et₂N⁺=SF₂ BF₄⁻ (diethylaminodifluorosulfinium tetrafluoroborate) | 205 | 1260 |
| 22 | morpholino-N⁺=SF₂ BF₄⁻ | 243 | 773 |
| 23 | (iPr)(Me)N⁺=SF₂ BF₄⁻ | 258 | 472 |
| 24 | (MeOCH₂CH₂)₂N⁺=SF₂ BF₄⁻ | 183 | 610 |
| 25 | pyrrolidinyl-N⁺=SF₂ BF₄⁻ | 198 | 1105 |
| 26 | PhN(Me)⁺=SF₂ (BF₄⁻ implied) | 186 | 714 |
| 27 | (2-pyridyl)N(Me)⁺=SF₂ | 144 | 802 |
| 28 | Et₂N⁺=SF₂ TfO⁻ | 161 | 1028 |
| 29 | morpholino-N⁺=SF₂ TfO⁻ | 189 | 441 |

More rigorous thermal safety assessments were performed by Accelerated Rate calorimetry (ARC) and comparing results of diethylaminodifluorosulfinium tetrafluoroborate and morpholinodifluorosulfinium tetrafluoroborate with commercially available samples of DAST and Deoxo-Fluor. Thus, both DAST and Deoxo-Fluor showed a raw onset of set-accelerated decomposition at 60° C. whereas diethylaminodifluorosulfinium tetrafluoroborate and morpholinodifluorosulfinium tetrafluoroborate onsets were detected at 119° C. and 141° C. respectively, exemplifying a significant increase in margin safety.

As mentioned in the historical background, Pashinnik et al. reported the deoxofluorination of an allylic alcohol using morpholinodifluorosulfinium tetrafluoroborate in acetonitrile and report a 85% yield of the corresponding fluoride as a mixture of epimers. This combination of reagent and solvent was tried on alternative alcohols to assess the potential scope of such salts from a broader perspective. Unexpectedly, geraniol led to an intractable mixture, whereas hydrocinnamyl alcohol provided N-acetyl-3-phenylpropylamine as the major product (example 30) via a Ritter-type reaction with the acetonitrile. Thus, acetonitrile is incompatible under these reaction conditions. However, by using dichloromethane as solvent, we surprisingly found that diethylaminodifluorosulfinium tetrafluoroborate did convert hydrocinnamyl alcohol into the desired fluoride, albeit sluggishly in 32% yield (example 31). Surprisingly, the addition of exogenous fluoride sources greatly improved the fluorination of alcohols. For example, the reagent combination of diethylaminodifluorosulfinium tetrafluoroborate and triethylamine trihydrofluoride in dichloromethane provided 78% conversion to 1-fluoro-3-phenylpropane (example 32). Retrospectively, these results show that reactions with disubstitutedaminodifluorosulfinium salts alone do not provide sufficient fluoride ions for conversion to the desired fluorinated product, but that the addition of exogenous fluoride can overcome this deficiency. We observed that the order of addition of the substrate, fluorinating reagent (disubstitutedaminodifluorosulfinium salt) and promoter (triethylamine trihydrofluoride) is an important parameter in the conversion of alcohols to the corresponding fluoride. In fact, if the triethylamine trihydrofluoride is added last, then the conversion to the desired fluoride marginally increases to 39% (example 33). However, if the substrate is added last, the conversion increases to 84% (example 34).

Example 30

Deoxofluorination of 3-phenylpropanol Using Morpholinodifluorosulfinium Tetrafluoroborate in Acetonitrile To a stirred suspension of morpholinodifluorosulfinium tetrafluoroborate (362 mg, 1.5 mmol) in acetonitrile (3.0 mL) at room temperature was added 3-phenylpropanol (131 μL, 1.0 mmol). After 1.5 h, the reaction mixture was quenched at room temperature with a 5% aqueous sodium bicarbonate solution, stirred for 15 minutes, and the resulting mixture was extracted twice using dichloromethane. The organic phases were combined, dried over magnesium sulfate and filtered through a pad of silica gel. Solvents were evaporated and the resulting crude material was purified by silica gel flash chromatography using DCM/MeOH (100/1) to provide 3-phenylpropanol (25 mg, 19%) and N-acetyl-3-phenylpropylamine (33 mg, 25%) as clear oils. Characterization for the latter: 1H NMR (CDCl3, 300 MHz) δ 7.31-7.08 (m, 5H), 5.60 (brs, 1H), 3.25 (q, J=6.8 Hz, 2H), 2.63 (t, J=7.7 Hz, 2H), 1.91 (s, 3H), 1.76 (m, 2H); $^{13}$C NMR (CDCl3, 75 MHz) δ 170.1, 141.4, 128.5, 128.3, 126.0, 38.3, 33.3, 31.1, 23.3.

Example 31

Deoxofluorination of 3-phenylpropanol Using Diethylaminodifluorosulfinium Tetrafluoroborate in Dichloromethane To a suspension of diethylaminodifluorosulfinium tetrafluoroborate (687 mg, 3.0 mmol) in dichloromethane (3.0 mL) at room temperature and under nitrogen is added 3-phenylpropanol (262 μl, 2.0 mmol). The reaction mixture is stirred for 30 min then analyzed by HPLC (using m-xylene as internal standard) which shows a 32% conversion to 1-fluoro-3-phenylpropane. The product was identified by comparison with an authentic sample. $^1$H NMR (CDCl$_3$, 300 MHz) δ 7.34-7.19 (m, 5H), 4.47 (dt, $^2J_{H-F}$=47.3 Hz, $^3J_{H-H}$=5.9 Hz, 2H), 2.76 (t, 7.3 Hz, 2H), 2.11-1.95 (m, 2H); $^{19}$F NMR (CDCl$_3$, 282 MHz) δ −220.6 (tt, $^2J_{H-F}$=47.6 Hz, $^3J_{H-F}$=23.0 Hz, 2F); $^{13}$C NMR (CDCl$_3$, 75 MHz) δ 141.2, 128.6, 128.6, 126.1, 83.2 (d, $^1J_{C-F}$=165.4 Hz), 32.2 (d, $^2J_{C-F}$=20.2 Hz), 31.4 (d, $^3J_{C-F}$=5.6 Hz)

Example 32

Deoxofluorination of 3-phenylpropanol Using Diethylaminodifluorosulfinium Tetrafluoroborate and Triethylamine Trihydrofluoride in Dichloromethane Addition Order A To a solution of 3-phenylpropanol (262 µl, 2.0 mmol) and triethylamine trihydrofluoride (326 µL, 2.0 mmol) in dichloromethane (3.0 mL), at room temperature and under nitrogen, is added diethylaminodifluorosulfinium tetrafluoroborate (687 mg, 3.0 mmol). The reaction mixture is stirred for 60 min then analyzed by HPLC (using m-xylene as internal standard) which shows a 78% conversion to 1-fluoro-3-phenylpropane. The product was identified by comparison with an authentic sample.

Example 33

Deoxofluorination of 3-phenylpropanol Using Diethylaminodifluorosulfinium Tetrafluoroborate and Triethylamine Trihydrofluoride in Dichloromethane Addition Order B To a suspension of diethylaminodifluorosulfinium tetrafluoroborate (687 mg, 3.0 mmol) and triethylamine trihydrofluoride (326 µL, 2.0 mmol) in dichloromethane (3.0 mL), at room temperature and under nitrogen, is added 3-phenylpropanol (262 µl, 2.0 mmol). The reaction mixture is stirred for 30 min then analyzed by HPLC (using m-xylene as internal standard) which shows a 84% conversion to 1-fluoro-3-phenylpropane. The product was identified by comparison with an authentic sample.

Example 34

Deoxofluorination of 3-phenylpropanol Using Diethylaminodifluorosulfinium Tetrafluoroborate and Triethylamine Trihydrofluoride in Dichloromethane Addition Order C To a suspension of diethylaminodifluorosulfinium tetrafluoroborate (687 mg, 3.0 mmol) and 3-phenylpropanol (262 µl, 2.0 mmol) in dichloromethane (3.0 mL), at room temperature and under nitrogen, is added triethylamine trihydrofluoride (326 µL, 2.0 mmol). The reaction mixture is stirred for 15 min then analyzed by HPLC (using m-xylene as internal standard) which shows a 39% conversion to 1-fluoro-3-phenylpropane. The product was identified by comparison with an authentic sample.

The effect of the promoter on the fluorination of an alcohol was assessed by varying the HF:TEA ratio. Exemplified by the fluorination of 4-phenyl-2-butanol, all 1HF:TEA, 2HF:TEA and 3HF:TEA promoters allowed the desired transformation, but 2HF:TEA provided a greater conversion.

Example 35

Deoxofluorination of 4-phenyl-2-butanol Using Morpholinodifluorosulfinium Tetrafluoroborate and 3HF.TEA To a suspension of morpholinodifluorosulfinium tetrafluoroborate (362 mg, 1.5 mmol) and triethylamine trihydrofluoride (326 µL, 2.0 mmol) in dichloromethane (3.0 mL), at room temperature and under nitrogen, is added 4-phenyl-2-butanol (155 µl, 1.0 mmol). The reaction mixture is stirred for 30 min then analyzed by HPLC (using m-xylene as internal standard) which shows a 71% conversion to 2-fluoro-4-phenylbutane. The product was identified by comparison with an authentic sample; $^1$H NMR (CDCl$_3$, 300 MHz) δ 7.35-7.11 (m, 5H), 4.62 (dm, $^2J_{H-F}$=48.4 Hz, 1H), 2.89-2.49 (m, 2H), 2.14-1.63 (m, 2H), 1.31 (dd, $^3J_{H-F}$=23.8 Hz, $^3J_{H-H}$=6.3 Hz, 3H); $^{19}$F NMR (CDCl$_3$, 282 MHz) δ −174.4 (m, 1F); $^{13}$C NMR (CDCl$_3$, 75 MHz) δ 141.4, 128.3, 125.9, 89.9 (d, $^1J_{C-F}$=165.2 Hz), 38.6 (d, $^2J_{C-F}$=20.6 Hz), 31.3 (d, $^3J_{C-F}$=5.2 Hz) 20.9 (d, $^2J_{C-F}$=21.3 Hz).

Example 36

Deoxofluorination of 4-phenyl-2-butanol Using Morpholinodifluorosulfinium Tetrafluoroborate and 2HF.TEA To a suspension of morpholinodifluorosulfinium tetrafluoroborate (362 mg, 1.5 mmol), triethylamine trihydrofluoride (326 µL, 2.0 mmol) and triethylamine (139 µL, 1.0 mmol) in dichloromethane (3.0 mL), at room temperature and under nitrogen, is added 4-phenyl-2-butanol (155 µl, 1.0 mmol). The reaction mixture is stirred for 30 min then analyzed by HPLC (using m-xylene as internal standard) which shows a 81% conversion to 2-fluoro-4-phenylbutane. The product was identified by comparison with an authentic sample.

Example 37

Deoxofluorination of 4-phenyl-2-butanol Using Morpholinodifluorosulfinium Tetrafluoroborate and 1 HF.TEA To a suspension of morpholinodifluorosulfinium tetrafluoroborate (362 mg, 1.5 mmol), triethylamine trihydrofluoride (326 µL, 2.0 mmol) and triethylamine (557 µL, 4.0 mmol) in dichloromethane (3.0 mL), at room temperature and under nitrogen, is added 4-phenyl-2-butanol (155 µl, 1.0 mmol). The reaction mixture is stirred for 30 min then analyzed by HPLC (using m-xylene as internal standard) which shows a 57% conversion to 2-fluoro-4-phenylbutane. The product was identified by comparison with an authentic sample.

Other sources of ionic fluoride were also found to promote deoxofluorination of alcohols, such as tetrabutylammonium hydrogen difluoride and hydrogen fluoride pyridine (a mixture of ~70% of HF and ~30% of pyridine).

Example 38

Deoxofluorination of Cyclooctanol Using Diethylaminodifluorosulfinium Tetrafluoroborate and Tetrabutylammonium Hydrogen Difluoride To an ice-cold suspension of diethylaminodifluorosulfinium tetrafluoroborate (344 mg, 1.5 mmol) and tetrabutylammonium hydrogen difluoride (422 mg, 1.5 mmol) in dichloromethane (3.0 mL) under nitrogen is added cyclooctanol (132 µl, 1.0 mmol). The reaction mixture is allowed to warm to room temperature and stirred for 4 h. The reaction mixture is quenched at room temperature with a saturated aqueous ammonium chloride solution, stirred for 15 min, and the resulting mixture is extracted twice using dichloromethane. The organic phases are combined, dried over magnesium sulfate, filtered and concentrated. The crude product is passed through a pad of silica gel using pentane to provide the title compound (80 mg, 62%) of admixed with cyclooctene (2.3:1 ratio respectively) as a clear oil. Major compound: $^1$H NMR (CDCl$_3$, 300 MHz) δ 4.63 (dm, $2J_{H-F}$=45.9 Hz, 1H), 1.96-1.42 (m, 16H); $^{19}$F NMR (CDCl$_3$, 282 MHz) δ −159.7 (brs, 1F); $^{13}$C NMR (CDCl3, 75 MHz) δ 95.0 (d, 1JC-F=163.4 Hz), 32.3 (d, 2JC-F=21.7 Hz), 27.4, 25.3, 22.2 (d, 3JC-F=9.8 Hz).

Example 39

Deoxofluorination of Cyclooctonal Using Diethylaminodifluorosulfinium Tetrafluoroborate and Hydrogen Fluoride Pyridine To a stirred suspension of diethylaminodifluorosulfinium tetrafluoroborate (344 mg, 1.5 mmol) in dichloromethane (3.0 mL) at room temperature and in a Nalgen bottle were successively added Olah's reagent (a mixture of ~70% HF and ~30% pyridine, 78 µL, 3 mmol of HF) and cyclooctanol (132 µL, 1 mmol). After 17 h, the reaction mixture is quenched at room temperature with a 5% aqueous sodium bicarbonate solution, stirred for 15 minutes, and the resulting mixture is extracted twice using dichloromethane. The organic phases are combined, dried over magnesium sulfate and filtered through a pad of silica gel. Solvents are evaporated to provide the title compound (58 mg, 44%) admixed with cyclooctene and cyclooctanol (1:0.44:0.28 ratio respectively) as a clear oil. Major product: $^1$H NMR (CDCl$_3$, 300 MHz) δ 4.63 (dm, $^2J_{F-H}$=45.9 Hz, 1H), 1.96-1.42 (m, 16H); $^{19}$F NMR (CDCl$_3$, 282 MHz) δ −159.7 (brs, 1F); $^{13}$C NMR (CDCl$_3$, 75 MHz) δ 95.0 (d, $^1J_{C-F}$=163.4 Hz), 32.3 (d, $^2J_{C-F}$=21.7 Hz), 27.4, 25.3, 22.2 (d, $^3J_{C-F}$=9.8 Hz).

During the survey of various additives, we surprisingly found that DBU can also promote the deoxofluorinations of alcohols. In retrospect, this advantageous effect on the fluorination can be rationalized in that the base promotes the ejection of the requisite fluoride, and in this scenario, exogenous sources of fluoride are not required. As it is the case for the fluoride source promoters, we observed that the order of addition of the substrate, fluorinating reagent (disubstitutedaminodifluorosulfinium salt) and base promoter is an important parameter in the conversion of alcohols to the corresponding fluoride. For example, if the fluorinating reagent is added last, then the conversion of 3-phenylpropanol to the desired fluoride is 92%, whereas if 3-phenylpropanol is added last, the conversion to the corresponding fluoride is 76%.

Example 40

Deoxofluorination of 3-phenylpropanol Using Diethylaminodifluorosulfinium Tetrafluoroborate and DBU Addition Order A To a solution of 3-phenylpropanol (132 µl, 1.0 mmol) and DBU (224 µL, 1.5 mmol) in dichloromethane (1.5 mL), at room temperature and under nitrogen, is added diethylaminodifluorosulfinium tetrafluoroborate (344 mg, 1.5 mmol). The reaction mixture is stirred for 17 h then analyzed by HPLC (using m-xylene as internal standard) which shows a 92% conversion to 1-fluoro-3-phenylpropane. The product was identified by comparison with an authentic sample.

Example 41

Deoxofluorination of 3-phenylpropanol Using Diethylaminodifluorosulfinium Tetrafluoroborate and DBU Addition Order B To a suspension of diethylaminodifluorosulfinium tetrafluoroborate (344 mg, 1.5 mmol) and DBU (224 µL, 1.5 mmol) in dichloromethane (1.5 mL), at room temperature and under nitrogen, is added 3-phenylpropanol (132 µl, 1.0 mmol). The reaction mixture is stirred for 19 h then analyzed by HPLC (using m-xylene as internal standard) which shows a 76% conversion to 1-fluoro-3-phenylpropane. The product was identified by comparison with an authentic sample.

During the survey of various additives, we also found that wide variety organic and inorganic bases can also promote the deoxofluorinations of alcohols (examples 42-48; table 4).

Procedure for the fluorination of alcohols using various base promoters (examples 42-48): To an ice-cold solution of cyclooctanol (132 µl, 1.0 mmol) and base (1.5 mmol) in dichloromethane (3.0 mL) under nitrogen, is added diethylaminodifluorosulfinium tetrafluoroborate (344 mg, 1.5 mmol). The reaction mixture is allowed to warm to room temperature and stirred for 18 h. The reaction mixture is quenched at room temperature with a 10% aqueous HCl solution, stirred for 15 min, and the resulting mixture is extracted twice using dichloromethane. The organic phases were combined, dried over magnesium sulfate, filtered through a pad of silica gel and concentrated to provide the fluorocyclooctane of admixed with cyclooctene as a clear oil (refer to the following table for yields and product distribution).

TABLE 4

Deoxofluorination of cyclooctanol with various base promoters

| Example | Promoter | Yield % | Ratio fluoro:alcene |
|---|---|---|---|
| 42 | DBU | 85% | 3.2:1 |
| 43 | DBN | 80% | 5.4:1 |
| 44 | Hunig's base | 65% | 2.5:1 |
| 45 | DABCO | 62% | 3.7:1 |
| 46 | tetramethyl guanidine | 56% | 2.7:1 |
| 47 | imidazole | 67% | 3.3:1 |
| 48 | sodium hydride | 80% | 7.2:1 |

Diethylaminodifluorosulfinium tetrafluoroborate alone was incapable of fluorinating carbonyls. For example, when 4-t-butylcyclohexanone was treated with diethylaminodifluorosulfinium tetrafluoroborate in dichloromethane, no detectable conversion to 4-t-butyl-1,1-difluorocyclohexane was observed even after 4 days at room temperature. However, the fluorination of carbonyls was promoted by the presence of exogenous fluoride ion promoters, such as 3HF.TEA, 2HF.TEA and tetrabutylammonium hydrogen difluoride and Olah's reagent

Example 49

Deoxofluorination of 4-t-butylcyclohexanone Using Diethylaminodifluorosulfinium Tetrafluoroborate and 3HF.TEA To a suspension of diethylaminosulfinium tetrafluoroborate (593 mg, 2.6 mmol) in dichloromethane (10 mL) at room temperature is added 4-tert-butylcyclohexanone (200 mg, 1.3 mmol) and triethylamine trihydrofluoride (266 µl, 1.3 mmol). The reaction mixture is stirred for 4 hours, then an aqueous solution of sodium bicarbonate (5%) is added and stirring is continued for 30 minutes. The organic phase is isolated and dried with magnesium sulphate. The solution is diluted with pentane (10 mL) and the solution is passed through a pad of silica gel with pentane elution. Solvent are evaporated in vacuo to provide 4-t-butyl-1,1-difluorocyclohexane (120 mg, 53%) as a clear liquid, admixed with 3% of the corresponding vinyl fluoride. Major compound: $^1$H NMR (CDCl$_3$) 2.09-1.95 (m, 2H), 1.76-1.67 (m, 2H), 1.65-1.51 (m, 2H), 1.30-1.15 (m, 2H), 1.02-0.97 (s, 1H), 0.80 (s, 9H); $^{19}$F NMR (CDCl$_3$)-91.9 (d, J=232.6 Hz, 1F), −103.5 (dm, J=232.6 Hz, 1F).

An additional advantage of diethylaminodifluorosulfinium tetrafluoroborate over DAST and Deoxo-Fluor® became apparent in the deoxofluorination of 4-t-butylcyclohexanone. Typically, a major side reaction observed in the deoxofluorination of ketones is the production of the corresponding vinylfluoride. In fact, the reaction of DAST/HF and Deoxo-Fluor®/HF with 4-t-butylcyclohexanone was reported leading to 33% and 19% of vinylfluoride side-product, whereas diethylaminodifluorosulfinium tetrafluoroborate/3HF-Et$_3$N exhibited higher selectivity by leading to less than 3% of vinylfluoride using the same substrate.

We surprisingly observed that the carbonyl substrate, fluorinating reagent (disubstitutedaminodifluorosulfinium salt) and promoter (triethylamine trihydrofluoride) could be added in any order of addition to enable the geminal difluorination of cabonyls to occur.

Example 50

Deoxofluorination of 4-Carboethoxycyclohexanone Using Diethylaminodifluorosulfinium Tetrafluoroborate and Triethylamine Trihydrofluoride

Addition Order A

To a solution of 4-carbethoxy-cyclohexanone (159 µL, 1.0 mmol) and triethylamine trihydrofluoride (163 µL, 1.0 mmol) in dichloromethane (2.0 mL), at room temperature and under nitrogen, is added diethylaminodifluorosulfinium tetrafluoroborate (344 mg, 1.5 mmol) portionwise over 1.5 h. The reaction mixture was stirred 15 h, then quenched with a 5% aqueous sodium bicarbonate solution, stirred for 15 min, and the resulting mixture was extracted using dichloromethane. The organic phases were combined, dried over magnesium sulfate and filtered through a pad of silica gel. Solvents were evaporated to provide 144 mg of a mixture comprising 4-carbethoxy-1,1-difluorocyclohexane (71%), 4-carbethoxy-1-fluorocyclohex-1-ene (6%) and 4-carbethoxy-cyclohexanone (23%) as a clear oil; Major compound: $^1$H NMR (CDCl$_3$, 300 MHz) δ 4.11 (q, J=7.0 Hz, 2H), 2.53-1.61 (m, 9H), 1.23 (t, J=7.0 Hz, 3H); $^{19}$F NMR (CDCl$_3$, 282 MHz) δ −94.3 (d, $^2$J$_{F-F}$=237.5 Hz, 1F), −99.8 (d, $^2$J$_{F-F}$=237.4 Hz, 1F); $^{13}$C NMR (CDCl$_3$, 75 MHz) δ 174.2, 127.2 (t, $^1$J$_{C-F}$=241.6 Hz), 60.5, 40.5, 32.5 (t, $^2$J$_{C-F}$=24.3 Hz), 25.0, 14.1.

Example 51

Deoxofluorination of 4-carboethoxycyclohexanone Using Diethylaminodifluorosulfinium Tetrafluoroborate and Triethylamine Trihydrofluoride

Addition Order B

To a suspension of diethylaminodifluorosulfinium tetrafluoroborate (344 mg, 1.5 mmol) and triethylamine trihydrofluoride (163 µL, 1.0 mmol) in dichloromethane (1.5 mL), at room temperature and under nitrogen, is added dropwise a solution of 4-carbethoxy-cyclohexanone (159 µL, 1.0 mmol) in dichloromethane (1.5 mL) over 1.5 h. The reaction mixture was stirred 15 h, then quenched with a 5% aqueous sodium bicarbonate solution, stirred for 15 min, and the resulting mixture was extracted using dichloromethane. The organic phases were combined, dried over magnesium sulfate and filtered through a pad of silica gel. Solvents were evaporated to provide 150 mg of a mixture comprising 4-carbethoxy-1,1-difluorocyclohexane (77%), 4-carbethoxy-1-fluorocyclohex-1-ene (5%) and 4-carbethoxy-cyclohexanone (18%) as a clear oil.

Example 52

Deoxofluorination of 4-carboethoxycyclohexanone Using Diethylaminodifluorosulfinium Tetrafluoroborate and Triethylamine Trihydrofluoride

Addition Order C

To a suspension of diethylaminodifluorosulfinium tetrafluoroborate (344 mg, 1.5 mmol) and 4-carbethoxy-cyclohexanone (159 µL, 1.0 mmol) in dichloromethane (1.5 mL), at room temperature and under nitrogen, is added a solution of triethylamine trihydrofluoride (163 µL, 1.0 mmol) in dichloromethane (0.5 mL) dropwise over 1.5 h. The reaction mixture was stirred 15 h, then quenched with a 5% aqueous sodium bicarbonate solution, stirred for 15 min, and the resulting mixture was extracted using dichloromethane. The organic phases were combined, dried over magnesium sulfate and filtered through a pad of silica gel. Solvents were evaporated to provide 147 mg of a mixture comprising 4-carbethoxy-1,1-difluorocyclohexane (69%), 4-carbethoxy-1-fluorocyclohex-1-ene (4%) and 4-carbethoxy-cyclohexanone (27%) as a clear oil.

Example 53

Deoxofluorination of 4-carboethoxycyclohexanone Using Diethylaminodifluorosulfinium Tetrafluoroborate and Tetrabutylammonium Hydrogen Difluoride To an ice-cold suspension of diethylaminodifluorosulfinium tetrafluoroborate (458 mg, 2.0 mmol) and tetrabutylammonium hydrogen difluoride (463 mg, 2.0 mmol) in dichloromethane (3.0 mL) under nitrogen is added 4-carboethoxycyclohexanone (159 µl, 1.0 mmol). The reaction mixture is allowed to warm to room temperature and stirred for 4 h. The reaction mixture is quenched at room temperature with a saturated aqueous ammonium chloride solution, stirred for 15 min, and the resulting mixture is extracted twice using dichloromethane. The organic phases are combined, dried over magnesium sulfate, filtered and concentrated. The crude product is passed through a pad of silica gel using pentane to provide 1-carboethoxy-4,4-difluorocyclohexane (130 mg, 68%) as a clear oil.

Example 54

Deoxofluorination of 4-t-butylcyclohexanone Using Diethylaminodifluorosulfinium Tetrafluoroborate and 2HF.TEA To a mixture of diethylaminosulfinium tetrafluoroborate (344 mg, 1.5 mmol), triethylamine trihydrofluoride (326 µl, 2.0 mmol) and triethylamine (139 µl, 1.0 mmol) in dichloromethane (3.0 mL) at room temperature is added 4-tert-butylcyclohexanone (154 mg, 1.0 mmol). The reaction mixture is stirred for 22 hours, then an aqueous solution of sodium bicarbonate (5%) is added and stirring is continued for 15 minutes. The phases are separated and the aqueous layer is extracted twice using dichloromethane. The organic phases are combined and dried with magnesium sulphate. The solution is passed through a pad of silica gel with dichloromethane elution. Solvent are evaporated in vacuo to provide 4-t-butyl-1,1-difluorocyclohexane (160 mg, 91%) as a clear liquid, admixed with 0.8% of the corresponding vinyl fluoride.

Example 55

Deoxofluorination of Hydrocinnamaldehyde Using Diethylaminodifluorosulfinium Tetrafluoroborate and Olah's Reagent In a Nalgen bottle, is added 3-phenylpropionaldehyde (132 µL, 1.0 mmol) and Olah's reagent (a mixture of ~70% HF and ~30% pyridine, 78 µL, 3 mmol of HF) to dichloromethane (3.0 mL) at room temperature. After 15 min diethylaminodifluorosulfinium tetrafluoroborate (344 mg, 1.5 mmol) is added and stirring continued. After 17.5 h, the reaction mixture is quenched at room temperature with a 5% aqueous sodium bicarbonate solution, stirred for 15 minutes, and the resulting mixture is extracted twice using dichloromethane. The organic phases are combined and washed with 10% HCl. The organic phases are dried over magnesium sulfate and filtered through a pad of silica gel. Solvents are evaporated to provide the title compound (121 mg, 78%) admixed with 3-phenylpropionaldehyde (4.3:1 ratio respectively) as a clear oil. Major product: $^1$H NMR (CDCl$_3$, 300 MHz) δ 7.38-7.22 (m, 5H), 5.65 (tt, $^2J_{H-F}$=56.7 Hz, $^3J_{H-H}$=4.4 Hz, 1H), 2.82 (t, J=7.7 Hz, 2H), 2.20 (m, 2H). $^{19}$F NMR (CDCl$_3$, 282 MHz) δ −117.5 (dt, $^2J_{H-F}$=56.7 Hz, $^3J_{H-F}$=16.9 Hz, 1F); $^{13}$C NMR (CDCl$_3$, 75 MHz) δ 140.2, 128.9, 128.6, 126.7, 117.0 (t, $^1J_{C-F}$=238.9 Hz), 35.9 (t, $^2J_{C-F}$=20.5 Hz), 28.7 (t, $^3J_{C-F}$=6.1 Hz).

Deoxofluorinations using promoters could be applied to a variety of substrates under various conditions. In certain cases, initiating the reactions at colder temperatures led to less elimination side-products, while in other cases, conducting the reactions at elevated temperature led to greater conversion. The scope of this method also includes, and is not limited to aldehydes, hemiacetals and carboxylic acids.

Example 56

Deoxofluorination of (R)—N-Cbz-3-hydroxypyrrolidine

Starting at −78° C.

To a solution of (R)—N-Cbz-3-hydroxypyrrolidine (221 mg, 1.0 mmol) in dichloromethane (3.0 mL) cooled at −78° C. are successively added DBU (224 µL, 1.5 mmol) and diethylaminodifluorosulfinium tetrafluoroborate (344 mg, 1.5 mmol). After stirring under nitrogen for 30 min, the reaction mixture is allowed to warm to room temperature and stirred for 24 h. The reaction mixture is quenched with a 5% aqueous sodium bicarbonate solution, stirred for 15 min, and the resulting mixture is extracted twice with dichloromethane. The organic phases are combined, dried over magnesium sulfate and filtered through a pad of silica gel. Solvents are evaporated and the resulting crude material is purified by silica gel flash chromatography using hexanes/EtOAc (3/1) to afford the title compound (192 mg, 86%) admixed with N-Cbz-2,5-dihydropyrrole (6.9:1 ratio respectively) as a clear oil. Major product: $^1$H NMR (CDCl$_3$, 300 MHz) δ 7.37-7.26 (m, 5H), 5.15 (d, $^2J_{H-F}$=52.5 Hz, 1H), 5.08 (s, 2H), 3.79-3.46 (m, 4H), 2.24-1.91 (m, 2H); $^{19}$F NMR (CDCl$_3$, 282 MHz) δ −177.8 (m, 1F); $^{13}$C NMR (CDCl$_3$, 75 MHz) δ 154.9, 136.9, 128.7, 128.2, 128.1, 93.0 (d, $^1J_{C-F}$=176.8 Hz), 92.2 (d, $^1J_{C-F}$=176.2 Hz), 67.1, 53.0 (d, $^2J_{C-F}$=27.1 Hz), 52.7 (d, $^2J_{C-F}$=27.1 Hz), 44.2, 43.8, 32.4 (d, $^2J_{C-F}$=57.6 Hz), 32.1 (d, $^2J_{C-F}$=57.6 Hz).

Example 57

Deoxofluorination of 4-carboethoxycyclohexanone

In Refluxing DCE

To a solution of triethylamine trihydrofluoride (163 µL, 1.0 mmol) in 1,2-dichloroethane (2.0 mL) is added at room temperature morpholinodifluorosulfinium tetrafluoroborate (362 mg, 1.5 mmol) followed by 4-carbethoxy-cyclohexanone (159 µL, 1.0 mmol) and the reaction mixture is heated to reflux. After 2 h, the reaction mixture is cooled to room temperature and quenched with a 5% aqueous sodium bicarbonate solution, stirred for 15 min, and the resulting mixture is extracted twice using dichloromethane. The organic phases are combined, dried over magnesium sulfate and filtered through a pad of silica gel. Solvents are evaporated and the resulting crude material is purified by silica gel flash chromatography using pentane to provide the title compound (166 mg, 86%) admixed with 4-carbethoxy-1-fluorocyclohex-1-ene (15:1 ratio respectively) as a clear oil.

Example 58

Deoxofluorination of 3-phenylpropionaldehyde

To a solution of triethylamine trihydrofluoride (326 µL, 2.0 mmol) in dichloromethane (3.0 mL) at room temperature are successively added diethylaminodifluorosulfinium tetrafluoroborate (344 mg, 1.5 mmol) and 3-phenylpropionaldehyde (132 µL, 1.0 mmol). After 2 h, the reaction mixture is quenched at room temperature with a 5% aqueous sodium bicarbonate solution, stirred for 15 min, and the resulting mixture is extracted twice using dichloromethane. The organic phases are combined, dried over magnesium sulfate and filtered through a pad of silica gel. Solvents were evaporated and the resulting crude material is purified by silica gel flash chromatography using pentane to provide the title compound (119 mg, 76%) as a clear oil; $^1$H NMR (CDCl$_3$, 300 MHz) δ 7.38-7.22 (m, 5H), 5.65 (tt, $^2J_{H-F}$=56.7 Hz, $^3J_{H-H}$=4.4 Hz, 1H), 2.82 (t, J=7.7 Hz, 2H), 2.20 (m, 2H). $^{19}$F NMR (CDCl$_3$, 282 MHz) δ −117.5 (dt, $^2J_{H-F}$=56.7 Hz, $^3J_{H-F}$=16.9 Hz, 1F); $^{13}$C NMR (CDCl$_3$, 75 MHz) δ 140.2, 128.9, 128.6, 126.7, 117.0 (t, $^1J_{C-F}$=238.9 Hz), 35.9 (t, $^2J_{C-F}$=20.5 Hz), 28.7 (t, $^3J_{C-F}$=6.1 Hz).

Example 59

Deoxofluorination of 2,3,4,6-tetra-O-benzyl-D-glucopyranose

To a solution of 2,3,4,6-tetra-O-benzyl-D-glucopyranose (100 mg, 0.18 mmol) and DBU (44 µL, 0.28 mmol) in dichloromethane (0.5 mL) is added diethylaminodifluorosulfinium tetrafluoroborate (68 mg, 0.28 mmol) at room temperature and under nitrogen. After 90 min of stirring, the reaction mixture is quenched at room temperature with a 5% aqueous sodium bicarbonate solution, stirred for 15 min, and the resulting mixture is extracted twice using dichloromethane. The organic phases are combined, dried over magnesium sulfate and filtered through a pad of silica gel. Solvents are evaporated to provide 2,3,4,6-tetra-O-benzyl-D-glucopyranosyl fluoride (96 mg, 96%, β:α anomers in a 1.1:1 ratio respectively) as a foam. $^1$H NMR (CDCl$_3$, 300 MHz) δ 7.47-7.15 (m, 20H), 5.61 (dd, $^2J_{H\text{-}F}$=53.2 Hz, $^3J_{H\text{-}H}$=2.3 Hz, 0.48H, α-anomer), 5.31 (dd, $^2J_{H\text{-}F}$=51.8 Hz, $^3J_{H\text{-}H}$=6.4 Hz, 0.52H, β-anomer), 5.07-4.48 (m, 8H), 4.11-3.54 (m, 6H); $^{19}$F NMR (CDCl$_3$, 282 MHz) δ −138.0 (dd, $^1J_{F\text{-}H}$=53.4 Hz, $^2J_{F\text{-}H}$=10.6 Hz, β-F), −149.44 (dd, $^1J_{F\text{-}H}$=54.4 Hz, $^2J_{F\text{-}H}$=25.8 Hz, α-F); $^{13}$C NMR (CDCl$_3$, 75 MHz) δ 138.5, 138.3, 138.1, 137.9, 137.5, 128.6, 128.5, 128.2, 128.1, 128.0, 127.9, 127.8, 112.8 (d, $^1J_{C\text{-}F}$=215.2 Hz, β-anomer), 108.6 (d, $^1J_{C\text{-}F}$=228.7 Hz, α-anomer), 83.6, 83.4, 81.7, 81.5, 81.4, 79.5, 79.2, 77.5, 77.1, 77.0, 77.7, 75.9, 75.5, 75.2, 75.0, 74.9, 74.8, 74.5, 73.6, 73.5, 72.7, 68.4, 67.8.

Example 60

Deoxofluoration of 3-phenylpropanoic Acid Using Diethylaminosulfinium Tetrafluoroborate and Triethylamine Trihydrofluoride To a suspension of diethylaminosulfinium tetrafluoroborate (750 mg, 3.3 mmol) in dichloromethane (10 mL) at room temperature was added 3-phenylpropanoic acid (245 mg, 1.6 mmol) and triethylamine trihydrofluoride (266 µl, 1.6 mmol). The reaction mixture was stirred for 24 hours, then an aqueous solution of sodium bicarbonate (5%) was added and stirring was continued for 30 minutes. The organic phase was isolated and dried with magnesium sulphate. The solution was diluted with pentane (10 mL) and the solution was passed through a pad of silica gel with pentane elution. Solvent were evaporated in vacuum to provide 3-phenylpropanoyl fluoride (168 mg, 68%) as a clear liquid. $^1$H NMR (CDCl$_3$, 300 MHz) δ 7.30-7.17 (m, 5H), 2.96 (t, J=7.6 Hz, 2H), 2.79 (t, J=7.6 Hz, 2H); $^{19}$F NMR (CDCl$_3$, 282 MHz) δ 44.8 (s, 1F); $^{13}$C NMR (CDCl$_3$, 75 MHz) δ 163.0 (d, $^1J_{C\text{-}F}$=180.2 Hz), 139.1, 128.9, 128.5, 127.0, 34.7 (d, =50.7 Hz), 30.2.

Example 61

Deoxofluoration of Benzoic Acid Using Diethylaminosulfinium Tetrafluoroborate and DBU To a suspension of diethylaminosulfinium tetrafluoroborate (344 mg, 1.5 mmol) in dichloromethane (3.0 mL) at room temperature is added benzoic acid (122 mg, 1.0 mmol) and DBU (224 µl, 1.5 mmol). The reaction mixture is stirred for 4 hours, then an 10% aqueous solution of HCl is added and stirring is continued for 15 minutes. The resulting mixture is extracted twice using dichloromethane. The organic phases are combined, dried over magnesium sulphate, filtered and concentrated. The crude material is diluted with pentane and the solution is passed through a pad of silica gel with pentane elution. Solvent are evaporated in vacuum to provide benzoyl fluoride (90 mg, 74%) as a clear liquid. $^1$H NMR (CDCl$_3$, 300 MHz) δ 7.94 (d, J=7.8, 2H), 7.62 (t, J=7.3 Hz, 1H), 7.43 (t, J=8.2 Hz, 2H); $^{19}$F NMR (CDCl$_3$, 282 MHz) δ 17.5 (s, 1F); $^{13}$C NMR (CDCl$_3$, 75 MHz) δ 157.3 (d, $^1J_{C\text{-}F}$=344.3 Hz), 135.5, 131.5 (d, $^3J_{C\text{-}F}$=4.0 Hz), 129.2, 125.0 (d, $^2J_{C\text{-}F}$=60.4 Hz).

Besides dichloromethane and 1,2-dichloroethane, others type of solvents can be employed in deoxofluorination reactions, including but not limited to those used in the following examples and listed in tables 5 and 6.

Procedure for the fluorination of alcohols in various solvents (examples 62-67): To a mixture of the diethylaminodifluorosulfinium tetrafluoroborate (344 mg, 1.5 mmol), triethylamine trihydrofluoride (326 µL, 2.0 mmol) and triethylamine (139 µL, 1.0 mmol) in the solvent (3.0 mL), at room temperature and under nitrogen, is added cyclooctanol (132 µl, 1.0 mmol). The reaction mixture is stirred for 24 h, then quenched with a 5% aqueous sodium bicarbonate solution, stirred for 15 min, and the resulting mixture was extracted using pentane. The organic phases were combined, dried over magnesium sulfate and filtered through a pad of silica gel. Solvents were evaporated to provide fluorocyclooctane of admixed with cyclooctene as a clear oil (refer to the following table for yields and product distribution).

TABLE 5

Deoxofluorination of cyclooctanol in various solvents

| Experiment | Solvent | Yield | Fluoro:alkene ratio |
|---|---|---|---|
| 62 | dichloromethane | 60% | 3.4:1 |
| 63 | N-methyl-2-pyrrolidinone | 22% | 0.3:1 |
| 64 | ethyl acetate | 73% | 2.5:1 |
| 65 | acetonitrile | 45% | 1.7:1 |
| 66 | methyl t-butyl ether | 91% | 1.6:1 |
| 67 | toluene | 53% | 1.6:1 |

Procedure for the fluorination of carbonyls in various solvents (examples 68-69): To a mixture of the diethylaminodifluorosulfinium tetrafluoroborate (458 mg, 2.0 mmol) and triethylamine trihydrofluoride (163 µL, 1.0 mmol) in the solvent (2.0 mL), at room temperature and under nitrogen, is added 4-carboethoxycyclohexanone (159 µl, 1.0 mmol). The reaction mixture is stirred for 23 h, then quenched with a 5% aqueous sodium bicarbonate solution, stirred for 15 min, and the resulting mixture was extracted using pentane. The organic phases were combined, dried over magnesium sulfate and filtered through a pad of silica gel. Solvents were evaporated to provide 4-carbethoxy-1,1-difluorocyclohexane admixed with 4-carbethoxy-1-fluorocyclohex-1-ene as a clear oil (refer to the following table for yields and product distribution).

TABLE 6

Deoxofluorination of 4-carboethoxycyclohexanone in various solvents

| Experiment | Solvent | Yield | Difluoro:fluoroalkene ratio |
|---|---|---|---|
| 68 | dichloromethane | 72% | 18:1 |
| 69 | N-methyl-2-pyrrolidinone | 36% | 0.13:1 |
| 70 | ethyl acetate | 57% | 11.4:1 |

TABLE 6-continued

Deoxofluorination of 4-carboethoxycyclohexanone in various solvents

| Experiment | Solvent | Yield | Difluoro:fluoroalkene ratio |
|---|---|---|---|
| 71 | acetonitrile | 63% | 16:1 |
| 72 | methyl t-butyl ether | 73% | 8.8:1 |
| 73 | toluene | 44% | 11.4:1 |

All of the aforementioned aminodifluorosulfinium salts were capable of performing deoxofluorination of alcohols and carbonyls when promoted with $Et_3N\cdot 3HF$ according to either of the following procedures and summarized in the tables 7 and 8.

Procedure for the fluorination of alcohols (examples 74-84): To a suspension of the disubstituted aminodifluorosulfinium salt (1.5 mmol), triethylamine trihydrofluoride (326 μL, 2.0 mmol) and triethylamine (139 μL, 1.0 mmol) in dichloromethane (3.0 mL), at room temperature and under nitrogen, is added cyclooctanol (132 μl, 1.0 mmol). The reaction mixture is stirred for 19 h, then quenched with a 5% aqueous sodium bicarbonate solution, stirred for 15 min, and the resulting mixture was extracted using dichloromethane. The organic phases were combined, dried over magnesium sulfate and filtered through a pad of silica gel. Solvents were evaporated to provide fluorocyclooctane of admixed with cyclooctene as a clear oil (refer to the following table for yields and product distribution).

TABLE 7

Deoxofluorination of cyclooctanol using various disubstituted aminodifluorosulfinium salts

| Experiment | Disubstituted difluorosulfinium salt | Yield | Fluoro:alkene ratio |
|---|---|---|---|
| 74 | Et₂N⁺=SF₂ BF₄⁻ | 62% | 3.4:1 |
| 75 | morpholino-N⁺=SF₂ BF₄⁻ | 85% | 7.3:1 |
| 76 | iPr₂N⁺=SF₂ BF₄⁻ | 79% | 2.6:1 |
| 77 | (MeOCH₂CH₂)₂N⁺=SF₂ BF₄⁻ | 64% | 4.3:1 |
| 78 | pyrrolidino-N⁺=SF₂ BF₄⁻ | 68% | 2.4:1 |
| 79 | PhN(Me)⁺=SF₂ BF₄⁻ | 57% | 4.3:1 |
| 80 | 2-pyridyl-N(Me)⁺=SF₂ BF₄⁻ | 64% | 3.1:1 |
| 81 | PhCH₂N(Me)⁺=SF₂ BF₄⁻ | 98% | 4.7:1 |
| 82 | Et₂N⁺=SF₂ TfO⁻ | 86% | 1.3:1 |
| 83 | iPr₂N⁺=SF₂ TfO⁻ | 68% | 1.5:1 |
| 84 | morpholino-N⁺=SF₂ TfO⁻ | 73% | 1.9:1 |

Procedure for the fluorination of carbonyls (examples 85-96): To a suspension of disubstituted aminodifluorosulfinium salt (2.0 mmol) and triethylamine trihydrofluoride (163 μL, 1.0 mmol) in dichloromethane (2.0 mL), at room temperature and under nitrogen, is added 4-carboethoxy-cyclohexanone (159 μL, 1.0 mmol). The reaction mixture was stirred 20 h, then quenched with a 5% aqueous sodium bicarbonate solution, stirred for 15 min, and the resulting mixture was extracted using dichloromethane. The organic phases were combined, dried over magnesium sulfate and filtered through a pad of silica gel. Solvents were evaporated to provide 4-carbethoxy-1,1-difluorocyclohexane admixed with 4-carbethoxy-1-fluorocyclohex-1-ene as a clear oil (refer to the following table for yields and product distribution).

TABLE 8

Deoxofluorination of 4-carboethoxy-cyclohexanone using various disubstituted aminodifluorosulfinium salts

| Experiment | Disubstituted difluorosulfinium salt | Yield | Difluoro:fluoroalkene ratio |
|---|---|---|---|
| 85 | Et₂N⁺=SF₂ BF₄⁻ | 72% | 18:1 |

TABLE 8-continued

Deoxofluorination of 4-carboethoxy-cyclohexanone using various disubstituted aminodifluorosulfinium salts

| Experiment | Disubstituted difluorosulfinium salt | Yield | Difluoro: fluoroalkene ratio |
|---|---|---|---|
| 86 | (morpholino)N⁺=SF₂ BF₄⁻ | 84% | 24:1 |
| 87 | (dimethylamino)N⁺=SF₂ BF₄⁻ | 63% | 20:1 |
| 88 | (bis(2-methoxyethyl)amino)N⁺=SF₂ BF₄⁻ | 80% | 27:1 |
| 89 | (pyrrolidino)N⁺=SF₂ BF₄⁻ | 67% | 41:1 |
| 90 | (N-methylanilino)N⁺=SF₂ BF₄⁻ | 79% | 81:1 |
| 91 | (N-methyl-2-pyridylamino)N⁺=SF₂ BF₄⁻ | 65% | 24:1 |
| 92 | (N-methylbenzylamino)N⁺=SF₂ BF₄⁻ | 99% | >100:1 |
| 93 | (diethylamino)N⁺=SF₂ TfO⁻ | 78% | 1.7:1 |
| 94 | (dimethylamino)N⁺=SF₂ TfO⁻ | 84% | 1.7:1 |
| 95 | (morpholino)N⁺=SF₂ TfO⁻ | 77% | 1.7:1 |

Based on these studies, disubstitutedaminodifluorosulfinium salts are particularly efficient in activating alcohols and carboxylic acids towards nucleophilic displacement by fluorides. By extension, other types of nucleophile could be employed. In this context, activation of carboxylic acids followed by displacement with amines would lead to peptide and/or amides. Likewise, activation of an alcohol followed by displacement with a carboxylic acid, an azide or another nucleophile would serve as a surrogate to the Mitsonobu reaction. It is expected that disubstitutedaminodifluorosulfinium salts would also promote cyclodehydrative processes.

While the invention has been described in connection with specific embodiments thereof, it is understood that it is capable of further modifications and that this application is intended to cover any variation, use, or adaptation of the invention following, in general, the principles of the invention and including such departures from the present disclosure that come within known, or customary practice within the art to which the invention pertains and as may be applied to the essential features hereinbefore set forth, and as follows in the scope of the appended claims.

What is claimed is:

1. An isolated solid of a disubstituted-aminodifluorosulfinium tetrafluoroborate salt represented by the formula:

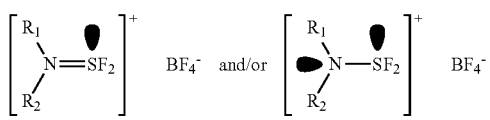

wherein $R_1$ and $R_2$ are both ethyl or $R_1$ and $R_2$ form together with the nitrogen atom to which they are attached:

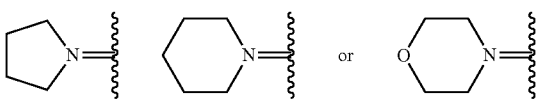

excluding:

diethylaminodifluorosulfinium tetrafluoroborate (needles; m.p. 74-76° C.);

piperidinodifluorosulfinium tetrafluoroborate (needles; m.p. 92-94° C.); and morpholinodifluorosulfinium tetrafluoroborate (prisms; m.p. 104-106° C.).

2. The isolated solid as defined in claim 1, selected from:

Diethylaminodifluorosulfinium tetrafluoroborate morphology type II;

Diethylaminodifluorosulfinium tetrafluoroborate morphology type III;

Diethylaminodifluorosulfinium tetrafluoroborate morphology type IV;

Diethylaminodifluorosulfinium tetrafluoroborate morphology type V;

Diethylaminodifluorosulfinium tetrafluoroborate morphology type VI; and

Morpholinodifluorosulfinium tetrafluoroborate morphology type II.

3. The isolated solid of claim 1, wherein $R_1$ and $R_2$ are both ethyl.

4. The isolated solid of claim 1, wherein $R_1$ and $R_2$ form together with the nitrogen atom to which they are attached:

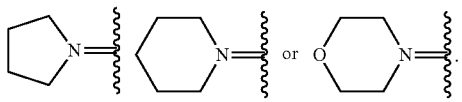

5. A method for preparing an isolated solid of disubstituted-aminodifluorosulfinium salts represented by the formula:

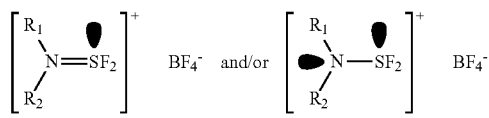

as defined in claim 1, comprising contacting unpurified disubstituted-aminosulfur trifluoride of formula $R_1R_2N$—$SF_3$ with a source of $BF_3$ or $HBF_4$, wherein $R_1$ and $R_2$ are as defined in claim 1.

6. The method according to claim 5 wherein the unpurified disubstituted-aminosulfur trifluoride is a crude reaction mixture.

7. The method according to claim 5, wherein the crude and unpurified disubstituted-aminosulfur trifluoride is prepared from a disubstituted-trimethylsilylamine and $SF_4$.

8. The method according to claim 5, which is conducted in the presence of a halocarbon solvent, an ether solvent or mixtures thereof.

9. The method according to claim 5, wherein the source of $BF_3$ is $BF_3$ gas or a complex selected from the group consisting of $BF_3$ etherate, $BF_3$ tetrahydrofuran complex and $BF_3$ acetonitrile complex.

10. The method according to claim 5, wherein the source of $HBF_4$ is a complex selected from the group consisting of $HBF_4$ etherate and $HBF_4$ dimethyl ether complex.

* * * * *